United States Patent
Walsh et al.

(10) Patent No.: US 12,059,360 B2
(45) Date of Patent: Aug. 13, 2024

(54) FUSION DEVICE

(71) Applicant: NewSouth Innovations Pty Limited, Sydney (AU)

(72) Inventors: William Robert Walsh, Maroubra (AU); Matthew Henry Pelletier, Matraville (AU)

(73) Assignee: NewSouth Innovations Pty Limited, Sydney (AU)

( * ) Notice: Subject to any disclaimer, the term of this patent is extended or adjusted under 35 U.S.C. 154(b) by 194 days.

(21) Appl. No.: 17/380,784

(22) Filed: Jul. 20, 2021

(65) Prior Publication Data

US 2022/0039966 A1    Feb. 10, 2022

Related U.S. Application Data

(63) Continuation of application No. 15/506,855, filed as application No. PCT/AU2015/000529 on Aug. 28, 2015, now Pat. No. 11,090,168.

(30) Foreign Application Priority Data

Aug. 29, 2014    (AU) ................................ 2014903442

(51) Int. Cl.
*A61F 2/44*      (2006.01)
*A61F 2/30*      (2006.01)

(52) U.S. Cl.
CPC ........ *A61F 2/4465* (2013.01); *A61F 2/30771* (2013.01); *A61F 2/4455* (2013.01); *A61F 2/447* (2013.01); *A61F 2002/30011* (2013.01); *A61F 2002/30153* (2013.01); *A61F 2002/30154* (2013.01); *A61F 2002/30156* (2013.01); *A61F 2002/30593* (2013.01); *A61F 2002/30772* (2013.01); *A61F 2002/30777* (2013.01); *A61F 2002/30785* (2013.01); *A61F 2002/30822* (2013.01); *A61F 2002/30828* (2013.01); *A61F 2002/30881* (2013.01);
(Continued)

(58) Field of Classification Search
CPC ................ A61F 2/4465; A61F 2/30771; A61F 2002/30153; A61F 2002/30154; A61F 2002/30156; A61F 2002/30777; A61F 2002/30785; A61F 2002/30828
See application file for complete search history.

(56) References Cited

U.S. PATENT DOCUMENTS

| | | |
|---|---|---|
| 6,206,924 B1 | 3/2001 | Timm |
| 6,482,233 B1 | 11/2002 | Aebi et al. |

(Continued)

FOREIGN PATENT DOCUMENTS

| | | |
|---|---|---|
| WO | 9512369 A1 | 5/1995 |
| WO | 9732547 A1 | 9/1997 |

OTHER PUBLICATIONS

European Patent Office Extended Search Report for Application No. 15836952.0 dated Mar. 21, 2018 (11 pages).
(Continued)

*Primary Examiner* — Nicholas J Plionis
(74) *Attorney, Agent, or Firm* — Michael Best & Friedrich LLP

(57) ABSTRACT

A device adapted to be positioned between two bone regions, the device comprising a body having a stabilising arrangement configured such that bone growing from one bone region toward the other engages the stabilising arrangement of the device.

18 Claims, 58 Drawing Sheets

(52) U.S. Cl.
CPC .............. *A61F 2002/30884* (2013.01); *A61F 2002/30891* (2013.01); *A61F 2002/30892* (2013.01); *A61F 2002/3093* (2013.01); *A61F 2310/00395* (2013.01); *A61F 2310/00592* (2013.01)

(56) References Cited

U.S. PATENT DOCUMENTS

| | | |
|---|---|---|
| 6,761,738 B1 | 7/2004 | Boyd |
| 8,142,508 B1 | 3/2012 | Bruffey et al. |
| 2005/0004671 A1 | 1/2005 | Ross et al. |
| 2006/0093646 A1 | 5/2006 | Cima et al. |
| 2006/0129242 A1 | 6/2006 | Bergeron et al. |
| 2008/0154378 A1 | 6/2008 | Pelo |
| 2011/0230970 A1* | 9/2011 | Lynn .................... A61F 2/4601 623/17.16 |
| 2011/0282392 A1 | 11/2011 | Murphy et al. |
| 2011/0282454 A1 | 11/2011 | Ullrich, Jr. et al. |
| 2011/0313532 A1 | 12/2011 | Hunt |
| 2013/0030529 A1 | 1/2013 | Hunt |
| 2013/0090735 A1* | 4/2013 | Mermuys ................ A61F 2/442 623/17.16 |
| 2014/0288649 A1 | 9/2014 | Hunt |
| 2014/0288650 A1 | 9/2014 | Hunt |
| 2017/0312089 A1 | 11/2017 | Duarte et al. |
| 2019/0076266 A1 | 3/2019 | Trudeau et al. |
| 2019/0099274 A1 | 4/2019 | Duarte |
| 2019/0183653 A1 | 6/2019 | Gregersen et al. |

OTHER PUBLICATIONS

International Search Report and Written Opinion or Application No. PCT/AU2015/000529 dated Sep. 30, 2015 (17 pages).
International Preliminary Report on Patentability for Application No. PCT/AU2015/000529 dated Dec. 23, 2016 (64 pages).

* cited by examiner

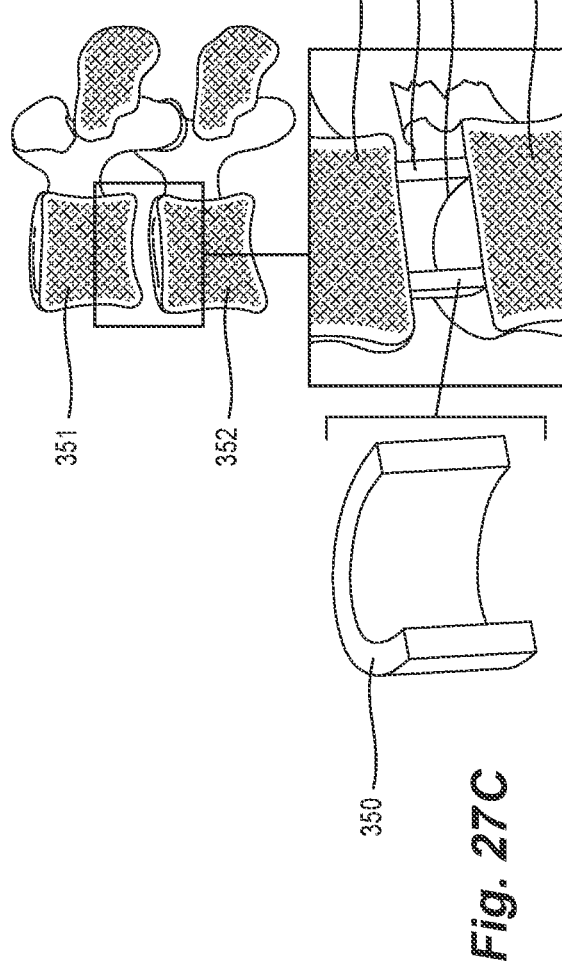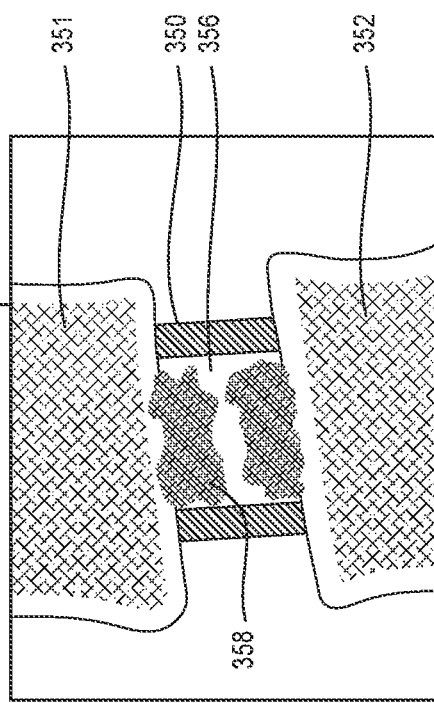

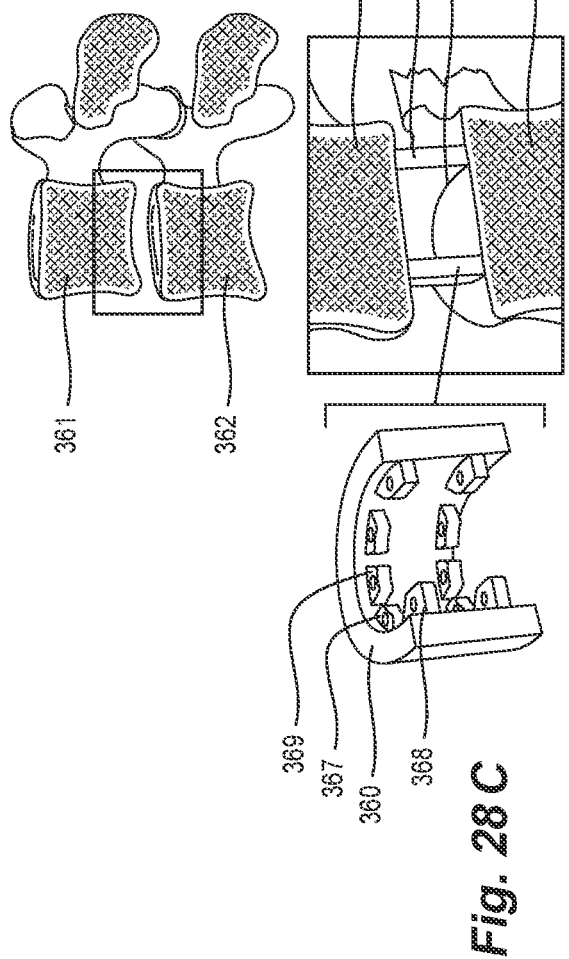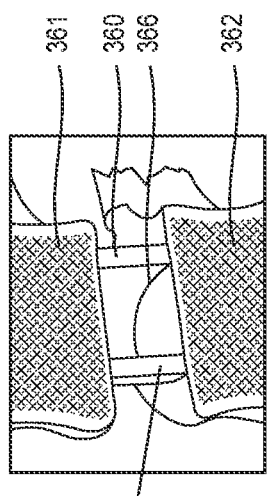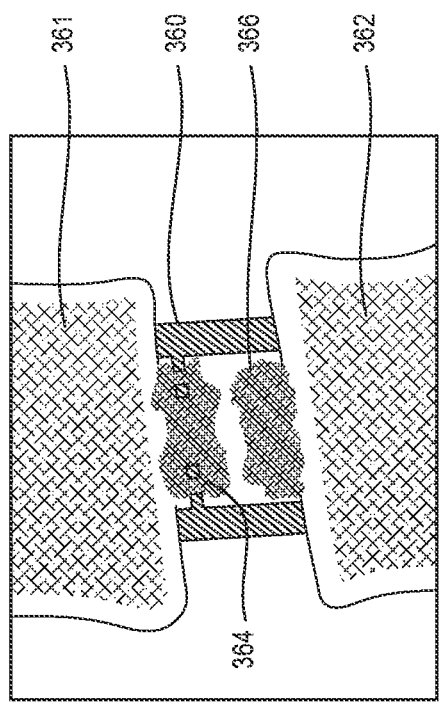

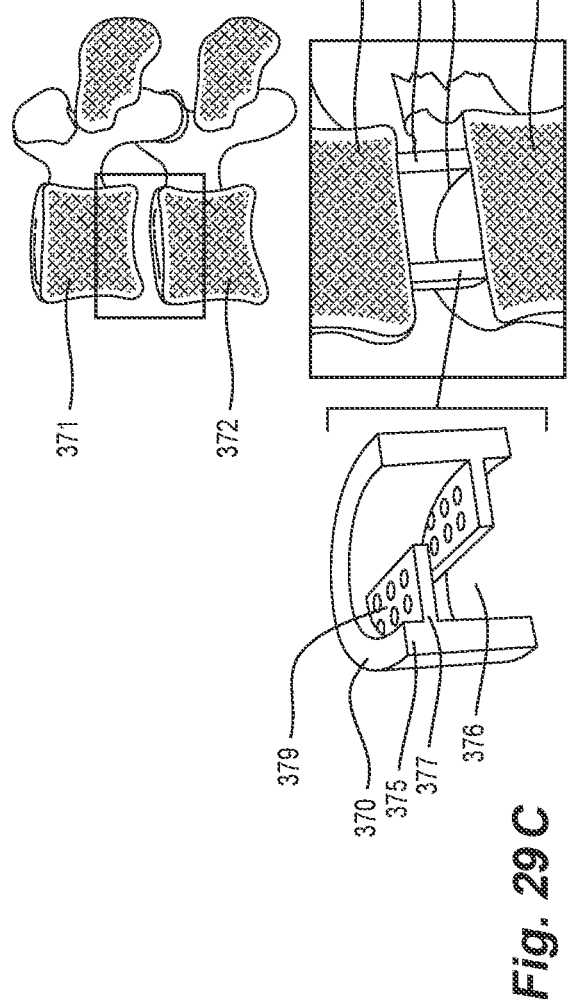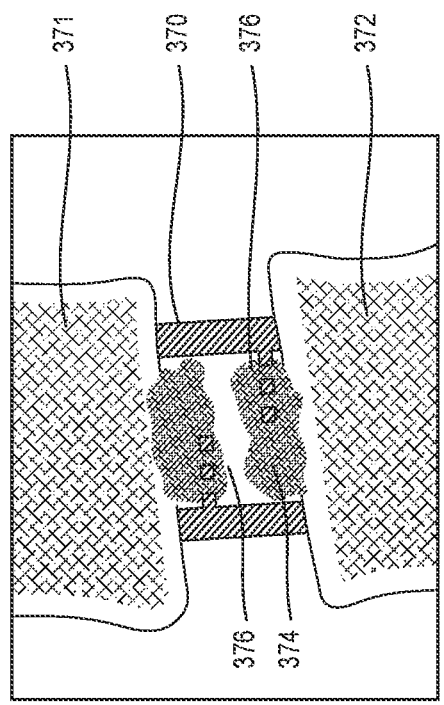
Fig. 29A
Fig. 29B
Fig. 29C
Fig. 29D

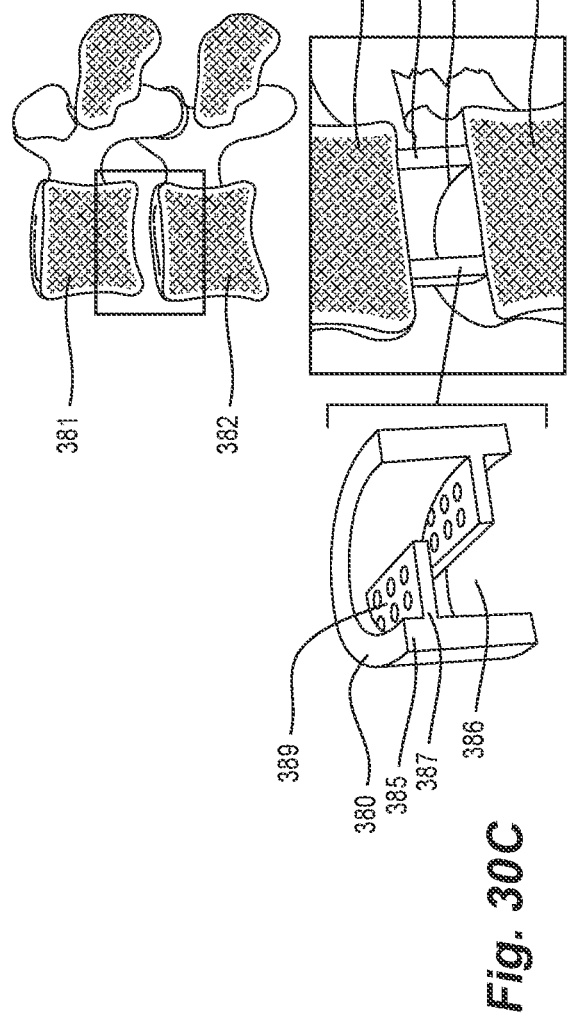
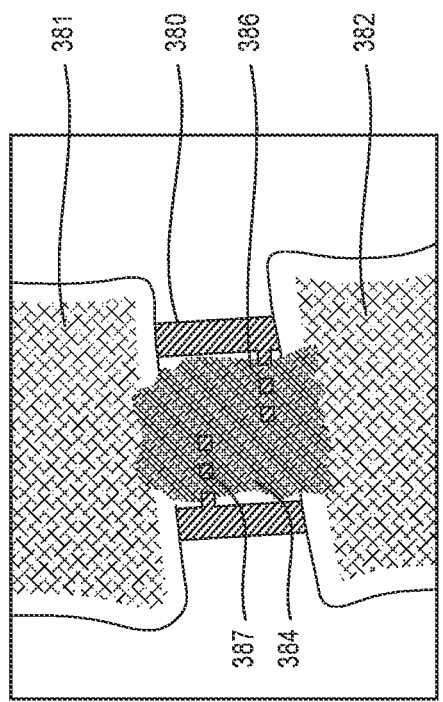

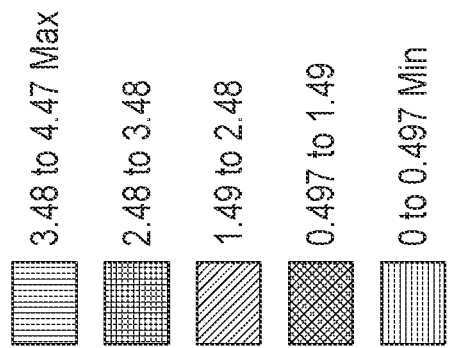
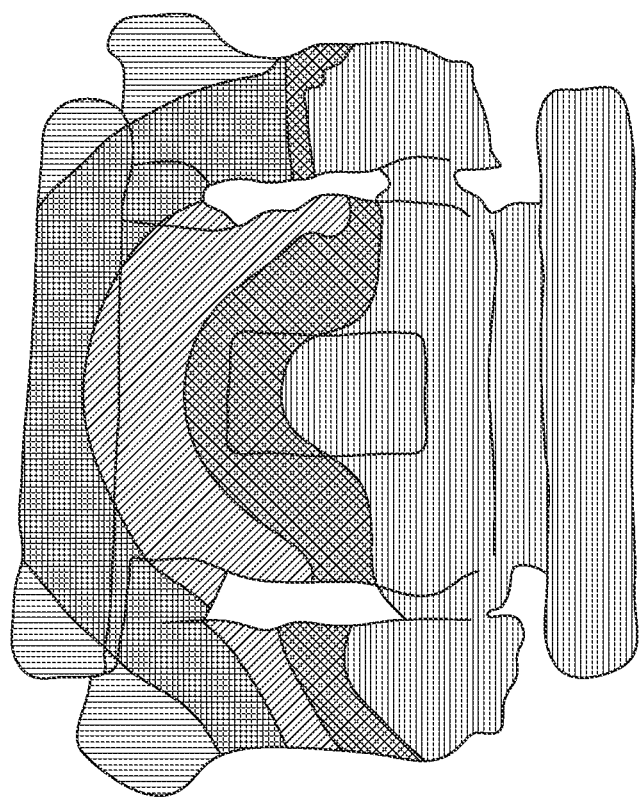
Fig. 39

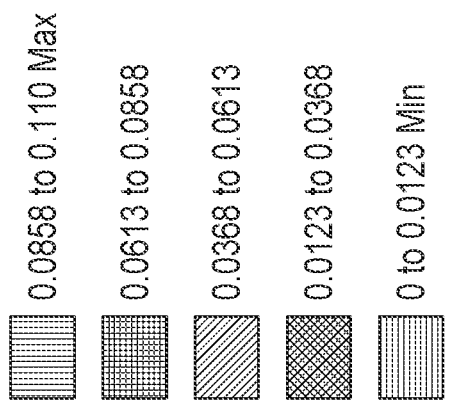
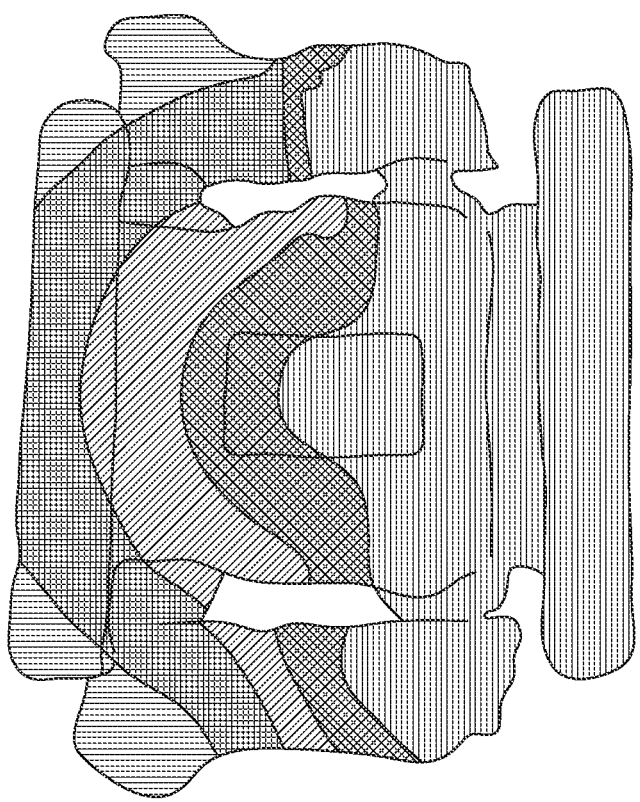
Fig. 53

ND DEVICE

CROSS-REFERENCE TO RELATED APPLICATIONS

This application is a continuation of U.S. patent application Ser. No. 15/506,855, filed on Feb. 27, 2017, which is the national phase of PCT/AU2015/000529, which claims priority to AU 2014903442. The foregoing applications are incorporated herein by reference.

TECHNICAL FIELD

This disclosure relates to fusion surgery and specifically to devices for promoting fusion or supporting bone regions for fusion. The devices have been described in relation to spinal fusion however people skilled in the art will be aware that the device has utility whenever fusion is indicated.

BACKGROUND

Fusion involves positioning a fusion device between two bone regions to support the bone regions and aid in fusion of the regions. Interbody fusion involves positioning an interbody fusion device or cage between two vertebral bodies to restore and maintain spine alignment and disc height and stabilize the spine which aids in fusion of the vertebrae. Commonly a cavity extends through the device. The surgeon deposits bone graft material within the cavity to stimulate or support growth of the bone through the device. The goal is to achieve mechanical stability. Ordinarily this occurs through fusion, as defined by the formation of a solid bone bridge between the two vertebrae.

SUMMARY OF THE DISCLOSURE

An improved device for facilitating mechanical stability between two bone regions is described. Stabilising arrangements are positioned on the device. These arrangements engage bone growing through, around, onto or adjacent the device. In use, the device is positioned between two bone regions. Bone growth that occurs through, around, onto or adjacent the stabilising arrangements of the device means that the bone engages with the device. This provides early mechanical stability and in some cases means union of bone to bone is not required for mechanical stability.

Disclosed is a device adapted to be positioned between two bone regions, the device comprising a body having a stabilising arrangement configured such that bone growing from one bone region toward the other engages the stabilising arrangement of the device.

Further disclosed is a method of promoting bone stability comprising positioning a device between bone regions, allowing the bone regions to grow around, into, through, or onto a stabilising region of the device such that the device is secured with respect to the bone region through ingrowth, ongrowth, throughgrowth or mechanical engagement of the bone region and newly formed bone onto the device.

In some forms the device is an interbody device and the bone regions are vertebral bodies. Henceforth the device will be discussed as an interbody device, although it will be clear to those skilled in the art that the devices have utility for use in stabilising and promoting fusion in ankles, wrists, toes, fingers and other locations where fusion is indicated.

The device allows a small amount of bone or connective tissue growth and ingrowth, throughgrowth, outgrowth or mechanical engagement around the stabilising arrangement of the interbody device to secure the bone with respect to the interbody device. This has the potential advantages of improving load distribution at the interface of the device, mechanically stabilising the interbody device and the spine, producing a stable and rigid spine more rapidly than with a conventional interbody device and allowing graft to be loaded such that the bone remodels and is maintained throughout the healing process. In some cases bone to bone union will not be required to provide bone stability as the bone growth regions from the vertebral body engages the interbody device mechanically by growing around the stabilising arrangement causing stability in more than one vector and rotational stability.

This can cause a rapid improvement in stability of the spine. In some cases the interbody device can incorporate no internal cavity or internal cavities that do not extend all the way through.

BRIEF DESCRIPTION OF THE FIGURES

Embodiments will now be described by way of example only, with reference to the accompanying drawings in which:

FIG. 27A provides a cross sectional view of a spine;

FIG. 27B provides an angled cross sectional view of a prior art device positioned between vertebrae in the spine of FIG. 27A;

FIG. 27C provides a cross sectional view of the prior art device of FIG. 27B;

FIG. 27D provides a cross sectional view of the device of FIG. 27B in use;

FIG. 28A provides a cross sectional view of a spine;

FIG. 28B provides an angled cross sectional view of one embodiment of a device of the disclosure positioned between vertebrae in the spine of FIG. 28A;

FIG. 28C provides a cross sectional view of the device of FIG. 28B;

FIG. 28D provides a cross sectional view of the device of FIG. 28B in use;

FIG. 29A provides a cross sectional view of a spine;

FIG. 29B provides an angled cross sectional view of one embodiment of a device of the disclosure positioned between vertebrae in the spine of FIG. 29A;

FIG. 29C provides a cross sectional view of the device of FIG. 29B;

FIG. 29D provides a cross sectional view of the device of FIG. 29B in use;

FIG. 30A provides a cross sectional view of a spine;

FIG. 30B provides an angled cross sectional view of one embodiment of a device of the disclosure positioned between vertebrae in the spine of FIG. 29A;

FIG. 30C provides a cross sectional view of the device of FIG. 29B;

FIG. 30D provides a cross sectional view of the device of FIG. 29B in use;

FIG. 39 shows the results of computational modeling for conventional plastic interbody device under global deflection in an anterior view;

FIG. 53 shows the results of computational modeling for a further embodiment of the present device under global deflection in an anterior view, titanium composition;

DETAILED DESCRIPTION OF EMBODIMENTS

Figure 1:
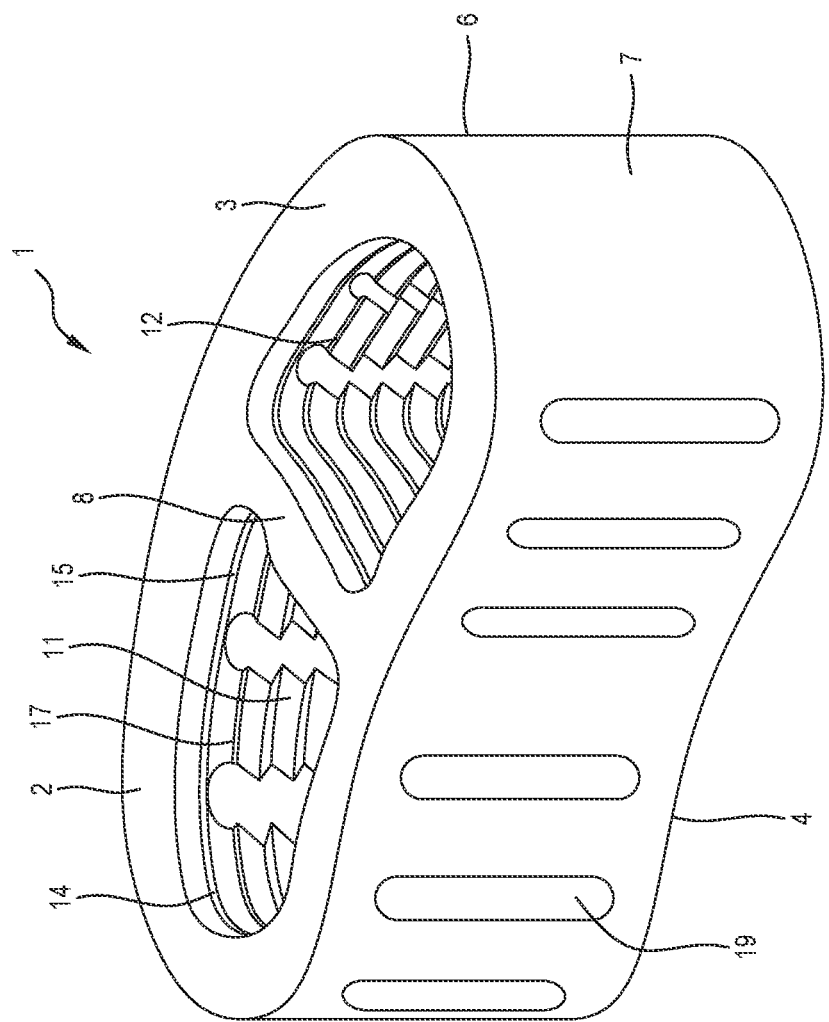
FIG. 1 provides a perspective view of one embodiment of the device of the disclosure.

In the following detailed description, reference is made to the accompanying drawings which form a part of the detailed description.

In some disclosed forms, disclosed is an interbody device adapted to be positioned between two vertebral bodies, the interbody device comprising a body having a stabilising arrangement configured such that bone growing from one vertebral body toward the other engages the stabilising arrangement of the interbody device.

The stabilising arrangements are configured to allow growth of bone that engages the stabilising arrangement to result in mechanical stability of the bone regions in relation to one another. In some cases this may reduce or eliminate the need for bone to bone union.

In some forms the body extends along an axis between two ends, each end being configured to be positioned in contact with or in the proximity of a vertebral body in use, the stabilising arrangement including a surface which is inclined with respect to the axis to allow for stabilising caused by bone or connective tissue growth around the stabilising arrangement.

In some forms each stabilising arrangement is located in proximity to each end.

In some forms the body includes an internal cavity. In some forms the stabilising arrangement is located inside the internal cavity. In some forms the internal cavity extends generally along the axis.

In some forms the body extends along an axis between two ends and the body is defined by a surface and the stabilising arrangement is a portion of the surface that is inclined with respect to the body axis.

In some forms the stabilising arrangement and the body are integral with one another.

In some forms the stabilising arrangement includes a shoulder about which the bone can grow, such that the bone and the shoulder provide mechanical stabilisation of the interbody device with respect to the vertebral body.

In some forms the stabilising arrangement comprises a projection extending from the body. In some forms the stabilising arrangement comprises a projection extending through the body.

In some forms the stabilising arrangement comprises a tab or rod extending from or through the body.

In some forms the stabilising arrangement is removable from the body.

In some forms the stabilising arrangement comprises a depression or aperture extending into the body.

In some forms the stabilising arrangement comprises a profiled surface.

In some forms, disclosed is a kit comprising an interbody device for positioning between vertebrae and a selection of stabilising arrangements adapted to engage with the interbody device and be positioned for use.

Further disclosed is a method of promoting spinal stability comprising: positioning an interbody device as defined in claim 1 between two vertebral bodies; depositing graft material proximal to the stabilising arrangement; allowing bone or connective tissues from each vertebral body to grow around, onto or into the stabilising arrangement to stabilise the interbody device with respect to each vertebral body.

Generally the application discloses a device including features that, when the device is positioned in proximity to a bone region or vertebral body, allow for ingrowth, throughgrowth, outgrowth, ongrowth or mechanical engagement of the device with respect to the bone region or vertebral body. The features are configured such that ingrowth outgrowth or ongrowth effects mechanical engagement in at least one plane. In a device having, for example, stabilizing arrangements positioned at top and bottom of the device and on both sides of the device, engagement of the bone with the top and bottom at any lateral position may result in effective mechanical engagement and spinal stability. In some cases, this mechanical engagement means that bone to bone union is not essential to provide the practical effects of fusion.

This has the advantage of improving stability between the bone region or vertebral body and the device which may result in bone or spinal stability at an earlier stage, improvement in load distribution and greater stability between the device and the bone region or vertebral body. The features include a stabilising arrangement in the form of a region that is angled with respect to the longitudinal axis of the interbody device. The stabilising arrangement may be in the form of surface profiles, shoulders or sloped regions. In other forms they may be in the form of plates, ridges, wires, or protrusions of various geometric arrangements extending from the device or in the form of depressions or apertures. In some forms the features are positioned in the interior of an internal cavity extending through the device. In some forms the features extend part or full way across the cavity. In some forms the features are removably attached with the device or removably extend through the device. In some forms the features may be inserted or engaged with the body of the device before or during surgery. In some forms the stabilizing arrangement comprises an opening or channel extending through the wall of the device, whether through a side wall or top wall. In some forms the arrangement further includes a tab or rod extending through the opening into the cavity in the device. In some forms the stabilizing arrangement comprises a plurality of protrusions extending inwardly from an interior surface of the cavity. In some forms the protrusions are positioned proximal an end of the device. In some forms the protrusions include holes extending therethrough. In some forms the stabilizing arrangement is a coating or includes a coating. The coating may be in the form of a porous material to allow for ingrowth, or in the form of a non-porous material to allow for ongrowth. The coating may be metal, ceramic or polymeric.

Referring now to FIG. 1, in one embodiment the disclosure provides an interbody device 1 comprising a body 2 extending between a first end 3 and a second end 4. The body 2 is generally sized and shaped to be positioned between vertebral bodies. In this embodiment the body comprises a curved wall 6 defined by an outer surface 7 and inner surface 12 extending between the first end 3 and the second end 4. A strut 8 extends longitudinally through the internal cavity to provide structural support.

In some forms the body 2 is composed of polyether ether ketone, polylactides or biocompatible polymers, carbonfibre composites, titanium, polyethylene, silicon nitride, or allograft, xenograft, autograft or other biologically compatible materials.

In this illustrated embodiment the body includes an internal cavity 11 extending between the two ends. The internal cavity 11 is defined by the inner surface 12 of the body. The inner surface 12 includes a stabilising arrangement 14 in the form of a profile 15 which means a portion of the surface 12 extends at an angle with respect to the overall movement of the surface between the ends. This profile 15 on the surface 12 forms a laterally extending surface 17 which is configured in use to engage with the bone or connective tissues as it grows.

In this embodiment apertures 19 extend through the body 2 from the internal cavity 11 to the outer surface 7. The apertures 19 are elongate extending along the body 2 between the ends 3, 4. The apertures 19 may have the benefit of allowing ingrowth or outgrowth and not isolating the bone graft. In some not illustrated forms the apertures include stabilising arrangements such as protrusions, profiles and the like.

In use, the interbody device is positioned between two vertebral bodies. Bone graft material is deposited within the internal cavity 11 to stimulate bone growth from the vertebral bodies. In this embodiment, bone growing into the internal cavity 11 of the body 2 may grow around the profile 15 causing bone ingrowth around the laterally extending surface 17. Specifically, the bone ingrowth or ongrowth may occur within 10 mm or preferably within 1 to 3 mm of either end 3, 4 of the body 2 providing spinal stability prior to engagement of a bridge of bone between the vertebral bodies. In some embodiments and cases bone to bone union will not be required to produce spinal stability.

Figure 2:
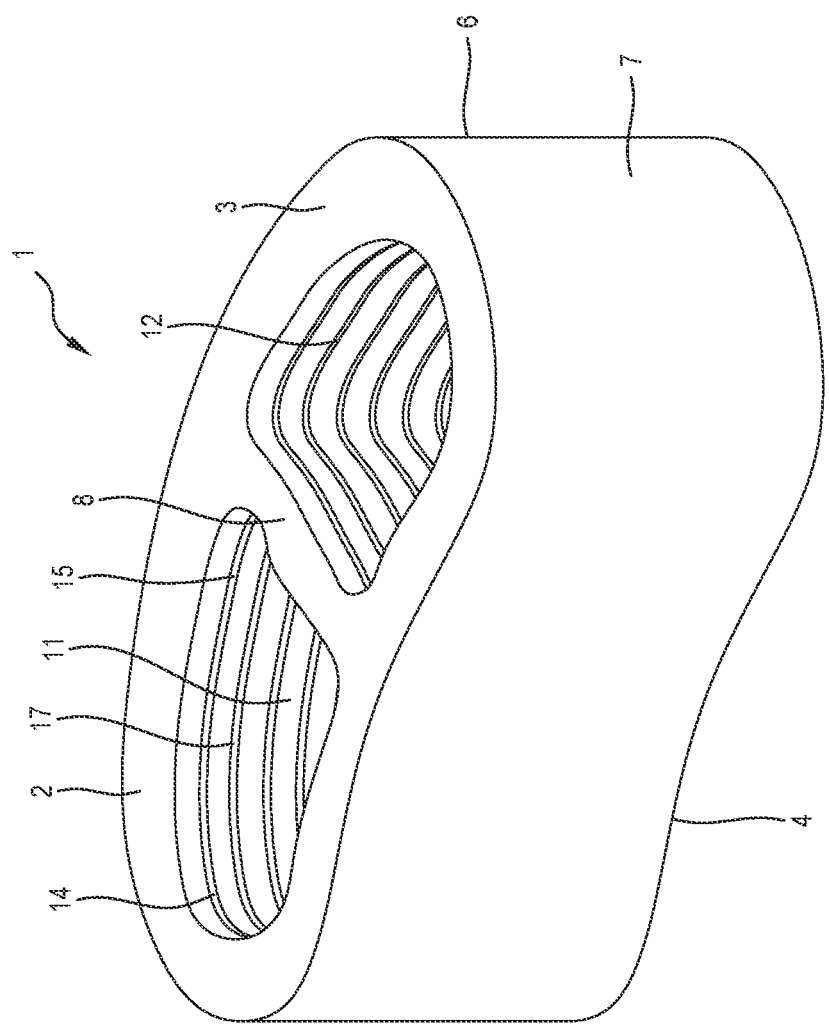
FIG. 2 provides a perspective view of a second embodiment of the device of the disclosure.

Referring now to FIG. 2, disclosed is an interbody device 1 comprising a body 2 extending between a first end 3 and a second end 4. As in the first embodiment, in this embodiment the body comprises a curved wall 6 extending between the first end 3 and the second end 4. A strut 8 extends through the internal cavity to provide structural support.

In this illustrated embodiment the body includes an internal cavity 11 extending between the two ends. The internal cavity 11 is defined by an internal surface 12 of the body. The internal surface 12 includes a stabilising arrangement 14 in the form of a profile 15 which means a portion of the surface 12 extends at an angle with respect to the overall movement of the surface between the ends. This profile 15 on the surface 12 forms a laterally extending surface 17.

Figure 3:
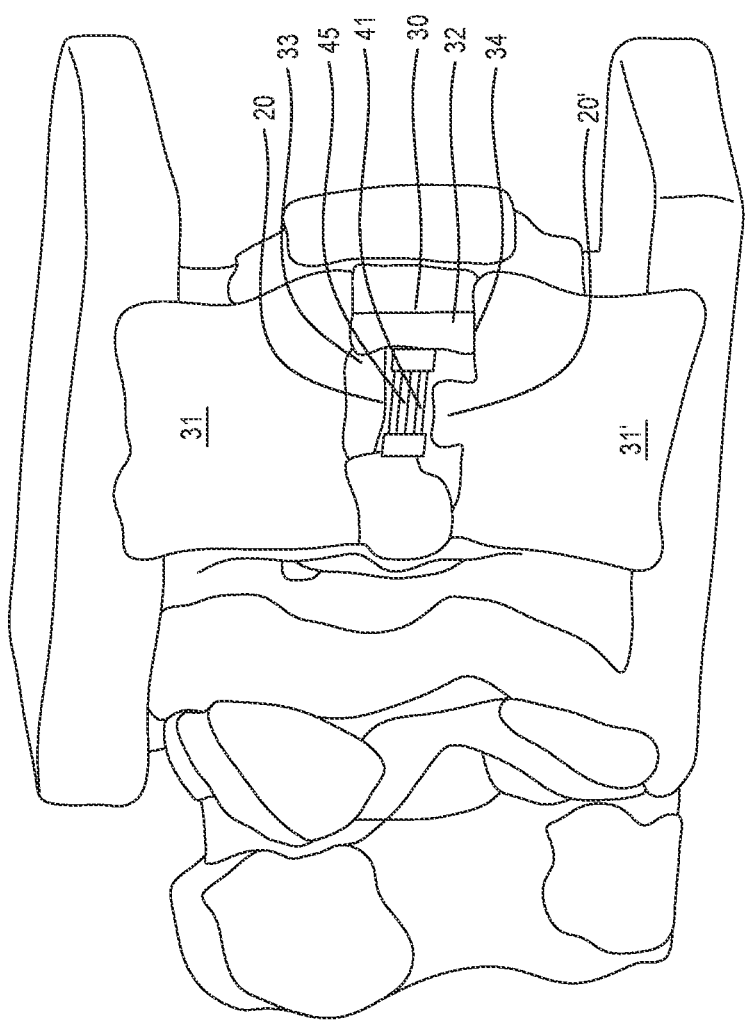
FIG. 3 provides an in situ view of one embodiment of the device of the disclosure.

Referring now to FIG. 3, disclosed is an interbody device 30, shown here in use as it would be used in vivo in cross-section. The device 30 is positioned between two vertebral bodies 31 and 31'. The device includes a body 32 extending between a first end 33 and a second end 34. The body includes an internal cavity 41 in which there are profiled surfaces 45. As shown in this figure, the bone growth 20 and 20' extends into the internal cavity 41 and around the profiled surface 45, resulting in ingrowth and outgrowth providing stability in more than one direction as well as mechanical engagement. In some forms this may result in stability prior to contact between bone growth extending downwardly from the top 20 and bone growth extending upwardly from the bottom 20'. In other cases the ingrowth around the profile will result in mechanical engagement for resistance of axial bending movement, axial rotation and for flexion and extension and any combination thereof.

Figure 4:
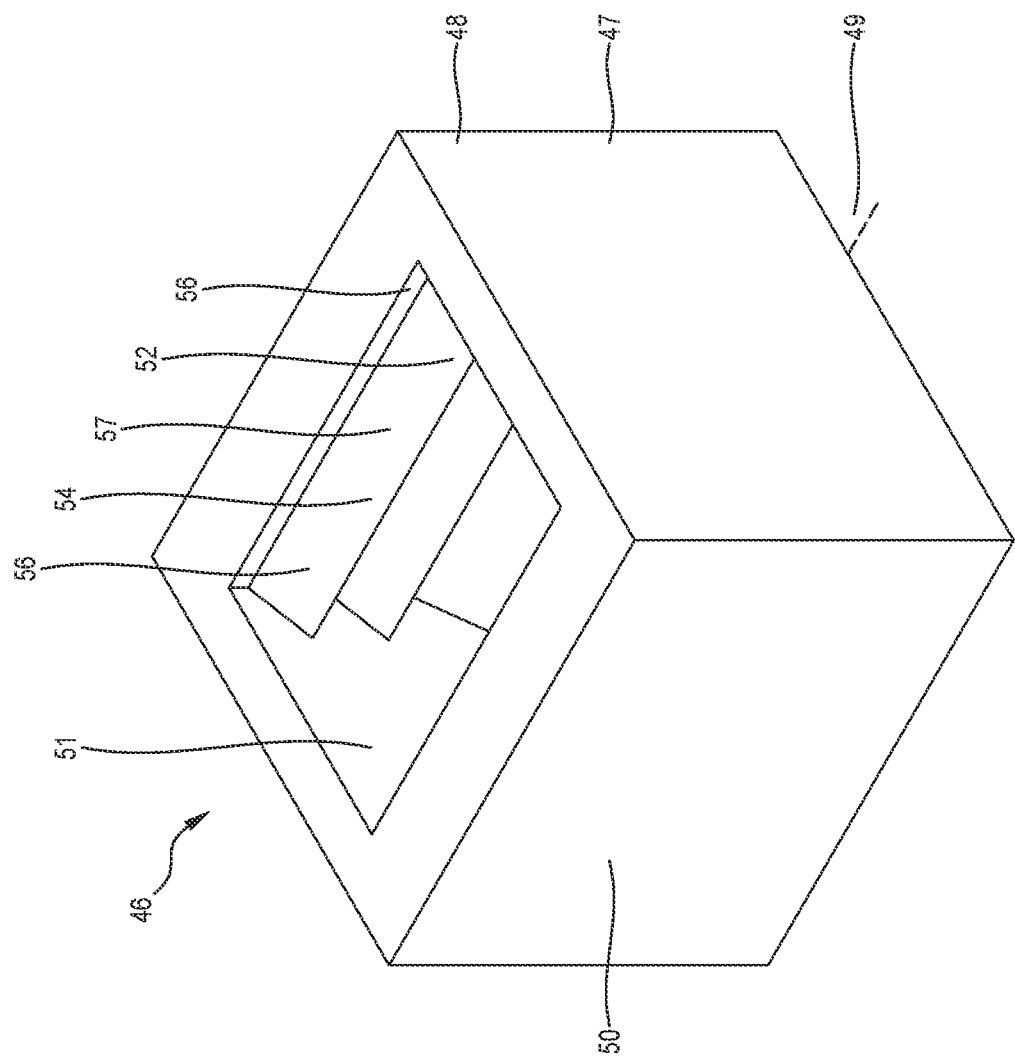
FIG. 4 provides a perspective view of a third embodiment of the device of the disclosure.

Referring now to FIG. 4, disclosed is an interbody device 46 comprising a body 47 extending between a first end 48 and a second end 49. In this embodiment the body comprises walls 50 extending between the first end 48 and the second end 49 and defining a generally square internal cavity 51.

In this illustrated embodiment the internal cavity 51 extends between the two ends. The internal cavity 51 is defined by an internal surface 52 of the body. The internal surface 52 includes a stabilising arrangement 54 in the form of a profile 56 in the form of inclined steps extending into the internal cavity 51. Thus a portion of the surface 52 extends at an angle with respect to the overall movement of the surface between the ends. This profile 56 on the surface 52 forms laterally extending surfaces 57 facing each end of the body.

Figure 5:
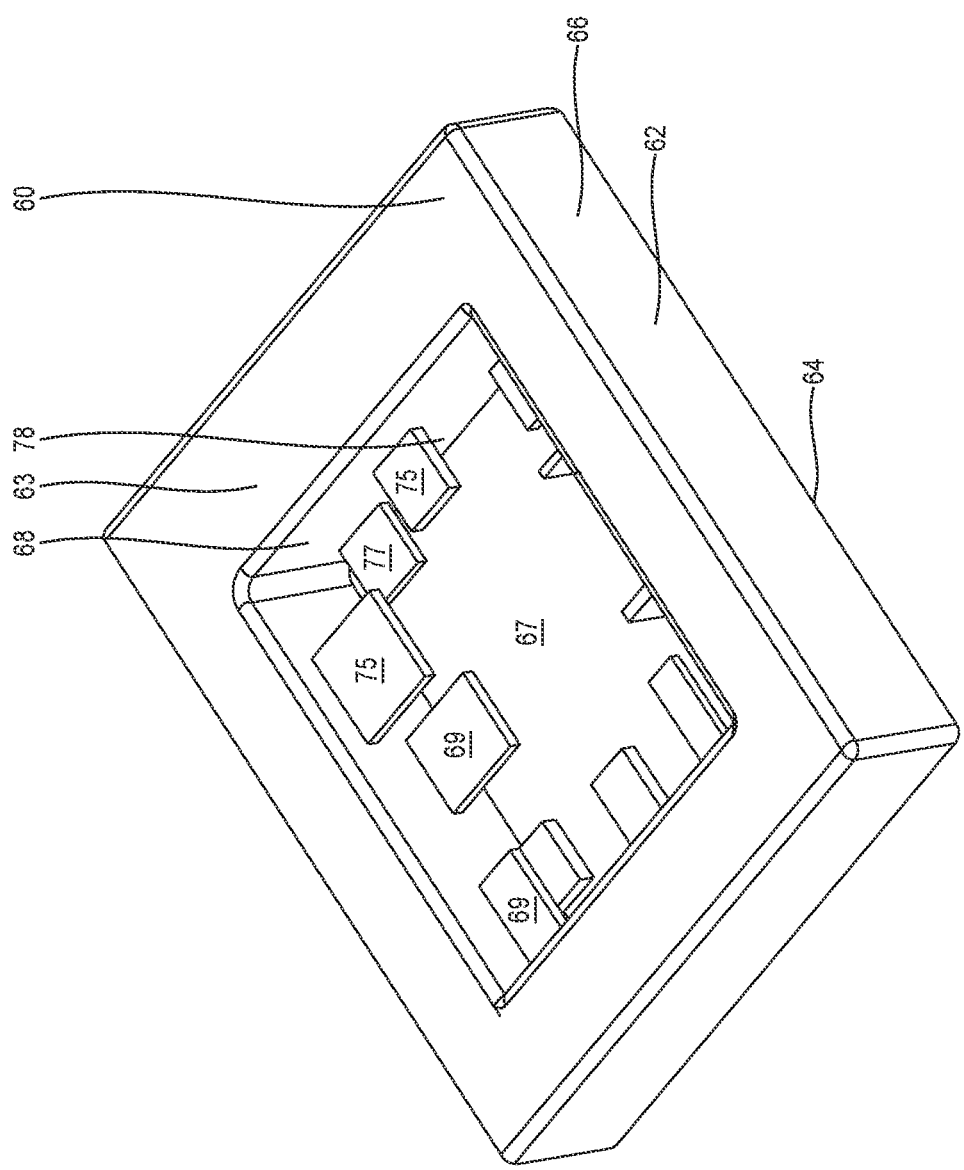
FIG. 5 provides a perspective view of a fourth embodiment of the device of the disclosure.

Referring now to FIG. 5, disclosed is an interbody device 60 comprising a body 62 extending between a first end 63 and a second end 64. In this embodiment the body 62 comprises a wall 66 defining an internal cavity 67 extending between the first end 63 and the second end 64.

In this illustrated embodiment the internal cavity 67 is defined by an internal surface 68 of the body. The internal surface 68 includes a stabilising arrangement 69 which is configured to allow bone or connective tissue growth to proceed around the stabilising arrangement 69. The stabilising arrangement is in the form of a series of plates 75 extending from the internal surface 68 into the internal cavity 67 and creating areas of ingrowth and stabilisation around which the bone can grow. A portion of the plates 75 extends laterally with respect to the internal surface and with respect to the overall movement of the surface between the ends or an axis extending between the ends. The lateral plates have upper faces 77 and lower faces 78 which are in a facing arrangement with the ends 63, 64 of the interbody device.

In use, the interbody device 60 is positioned between two vertebral bodies. Bone graft material is deposited within the internal cavity 67 to stimulate bone growth from the vertebral bodies. In this embodiment, bone growing into the internal cavity 67 of the body 62 may grow around the plates 75 causing mechanical engagement and hooking around the plates to provide stability in more than one vector. Specifically, the bone ingrowth or ongrowth may occur within 10 mm or preferably within 1 to 3 mm of either end 63, 64 of the body 62 providing spinal stability in at least one direction and in some cases in three dimensions prior to engagement of the bone. In some embodiments and cases bone to bone union will not be required to produce stability between the bones.

Figure 6:
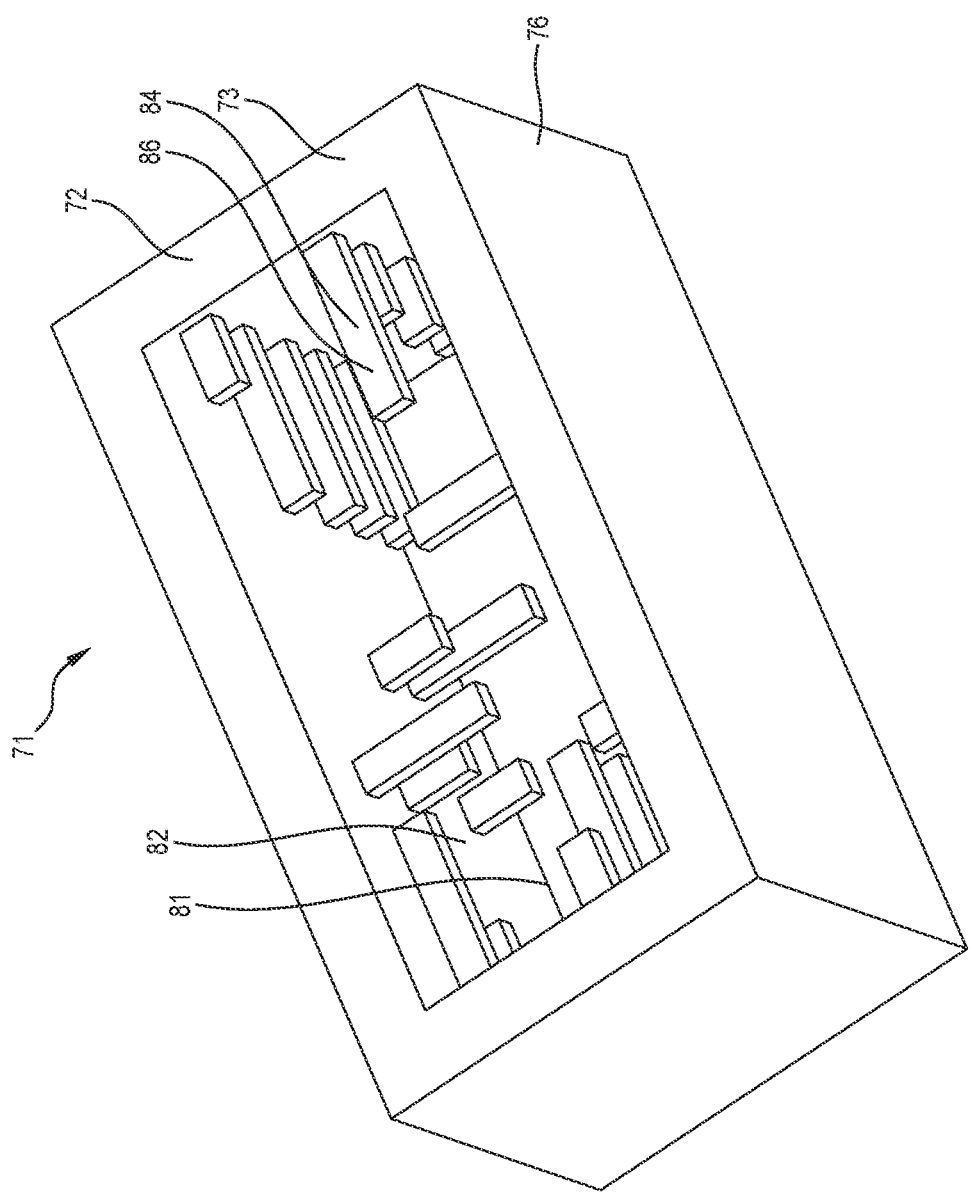
FIG. 6 provides a perspective view of a fifth embodiment of the device of the disclosure.

Referring now to FIG. 6, disclosed is an interbody device 71 comprising a body 72 extending between a first end 73 and a second end 74. The body comprises a walls 76 extending between the first end 73 and the second end 74.

In this illustrated embodiment the body includes an internal cavity 81 extending between the two ends. The internal cavity 81 is generally rectangular in cross section and is defined by an internal surface 82 of the walls 76 of the body. The internal surface 82 includes a stabilising arrangement 84 in the form of a plurality of tabs 86 extending from the internal surface 82 into the internal cavity 81. The tabs in this embodiment are generally elongate and extend varying lengths into the internal cavity 81. The tabs 86 include laterally extending faces which are in a facing relationship with the ends of the body.

Figure 7:
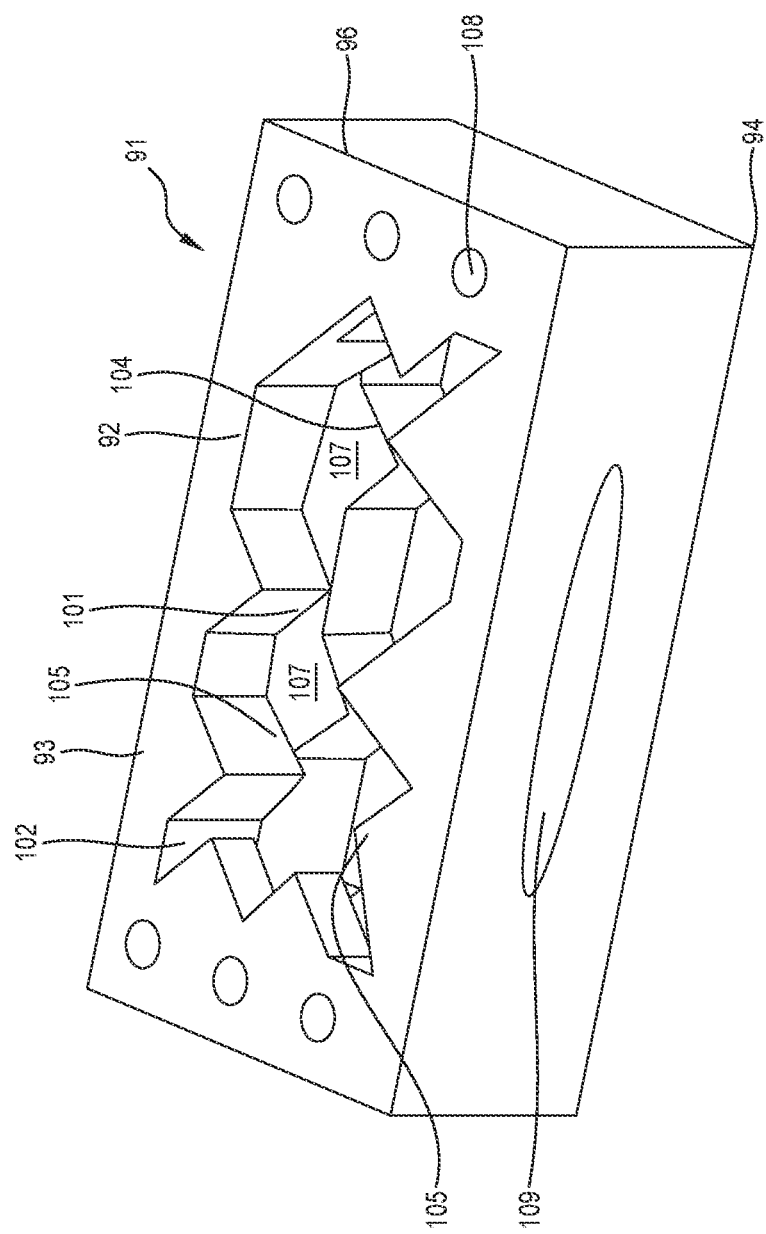
FIG. 7 provides a perspective view of a sixth embodiment of the device of the disclosure.

Referring now to FIG. 7, disclosed is an interbody device 91 comprising a body 92 extending between a first end 93 and a second end 94. The body 92 comprises walls 96 extending between the first end 93 and the second end 94.

In this illustrated embodiment the body includes an internal cavity 101 extending between the two ends. The internal cavity 101 is defined by an internal surface 102 of the walls 96 of the body. The internal surface 102 includes a stabilising arrangement 104 in the form of a series of projections and depressions 105 some of which are triangular in lateral cross section and extend from the walls 96 into the internal cavity 101 at intervals. In this form the projections and depressions 105 are offset with respect to one another. The projections 105 form a series of laterally extending surfaces 107 about which growth could occur.

The walls 96 include apertures 109 extending therethrough. The apertures 109 in this form are ovaloid and extend laterally. The walls further include longitudinally extending cavities 108 which allow for further bone ingrowth into the device body.

Figure 8:
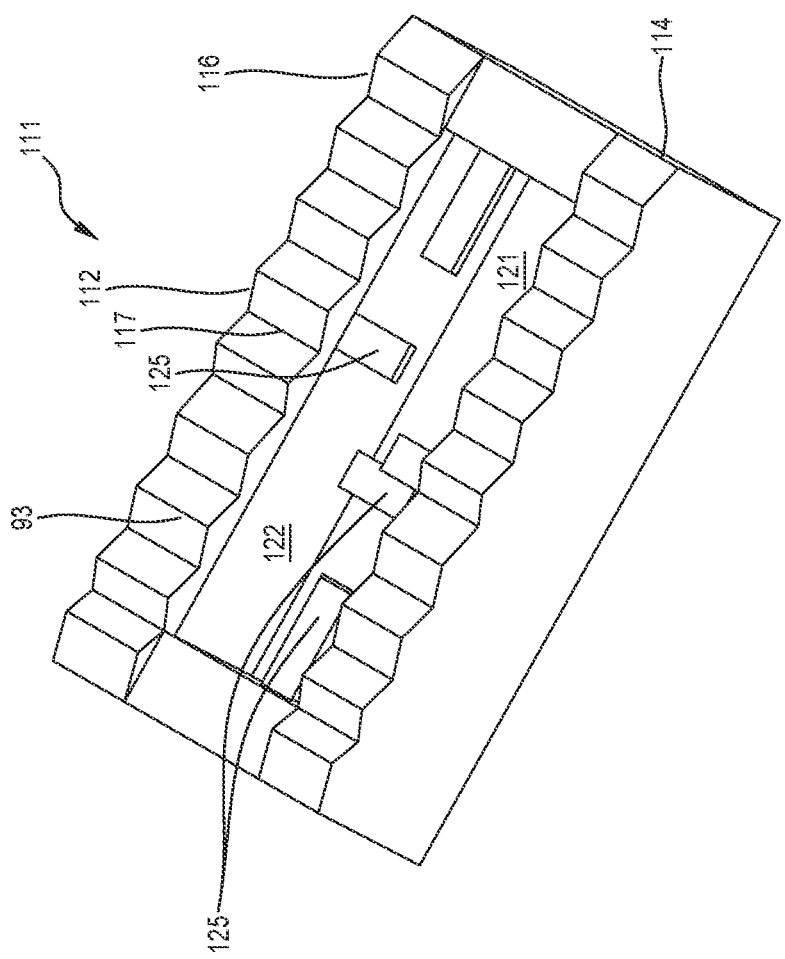
FIG. 8 provides a perspective view of a seventh embodiment of the device of the disclosure.

Referring now to FIG. 8, disclosed is an interbody device 111 comprising a body 112 extending between a first end 113 and a second end 114. The body comprises walls 116 extending between the first end 113 and the second end 114. The upper surface 115 of the first end 113 includes a profile 117 positioned at the top of a portion of the walls 116.

In this illustrated embodiment the body includes an internal cavity 121 extending between the two ends. The internal cavity 121 is defined by an internal surface 122 of the body. The internal surface 122 includes a stabilising arrangement 124 in the form of a series of tabs 125 which extend inwardly from the internal surface 122.

Figure 9:
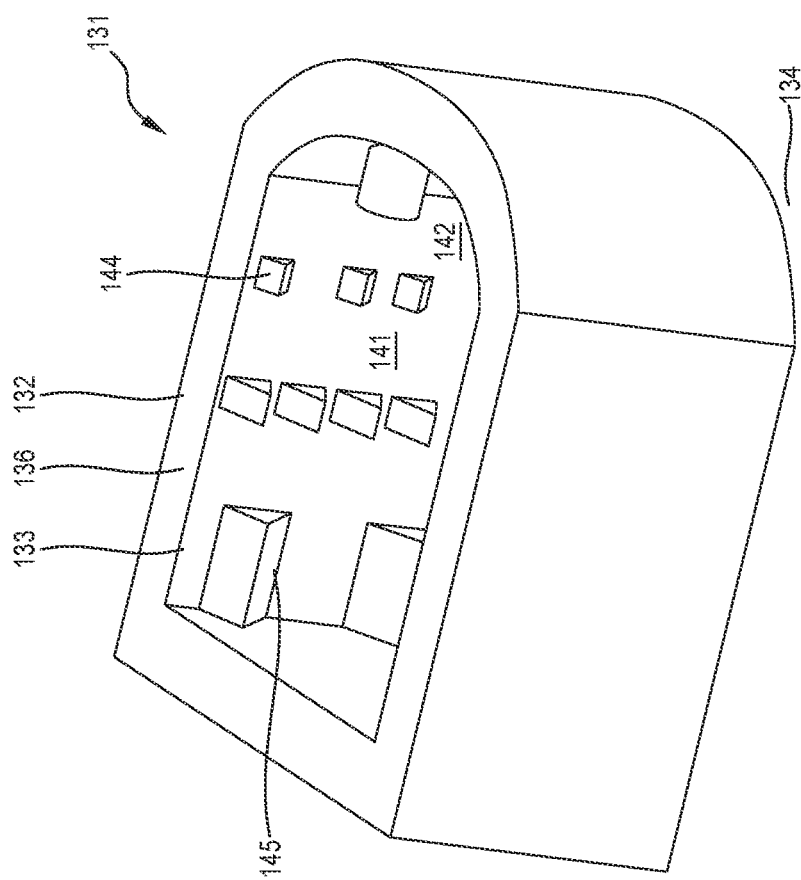
FIG. 9 provides a perspective view of an eighth embodiment of the device of the disclosure.

Referring now to FIG. 9, disclosed is an interbody device 131 comprising a body 132 extending between a first end 133 and a second end 134. The body comprises walls 136 extending between the first end 133 and the second end 134. A portion of the walls 136 is curved.

In this illustrated embodiment the body includes an internal cavity 141 extending between the two ends. The internal cavity 141 is defined by an internal surface 142 of the body. The internal surface 142 includes a stabilising arrangement 144 in the form of a series of projections 145 which extend inwardly from the internal surface 142. In this illustrated embodiment the projections 145 comprise a series of varied projections with triangular longitudinal cross-sections.

Figure 10:
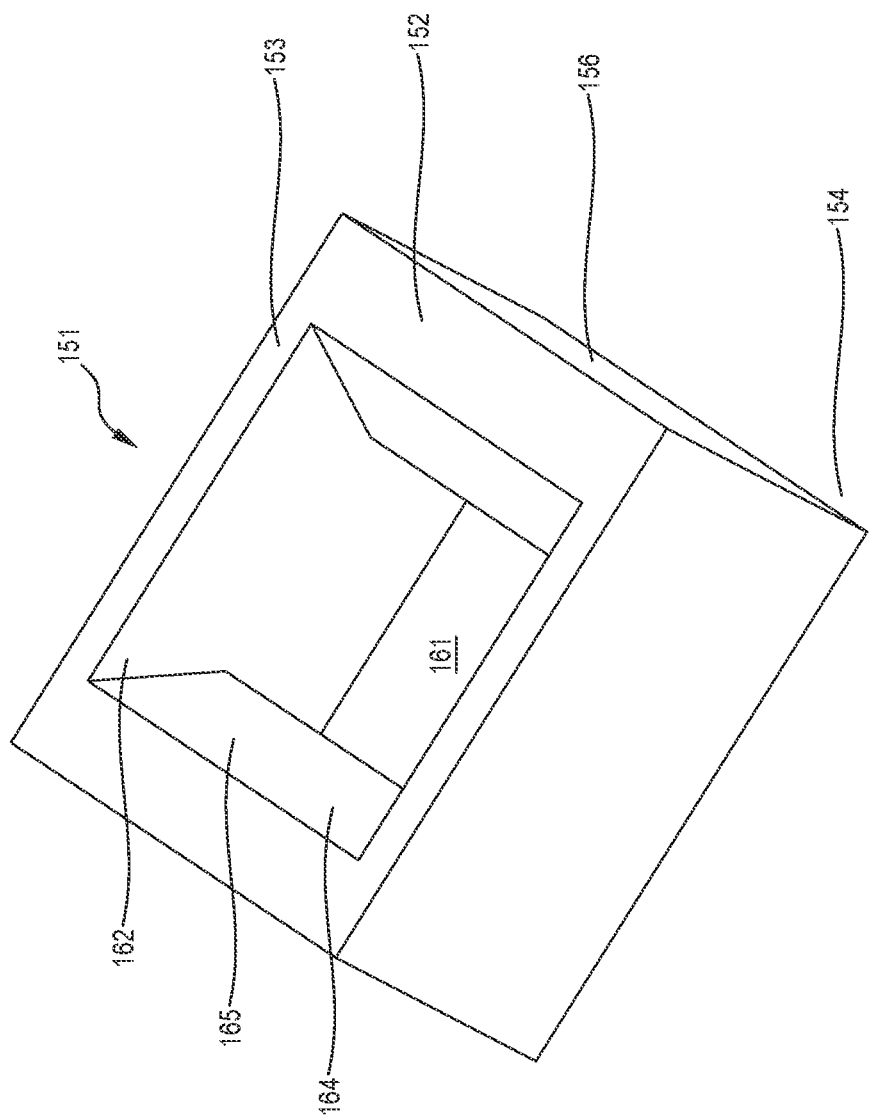
FIG. 10 provides a perspective view of a ninth embodiment of the device of the disclosure.
Figure 11:
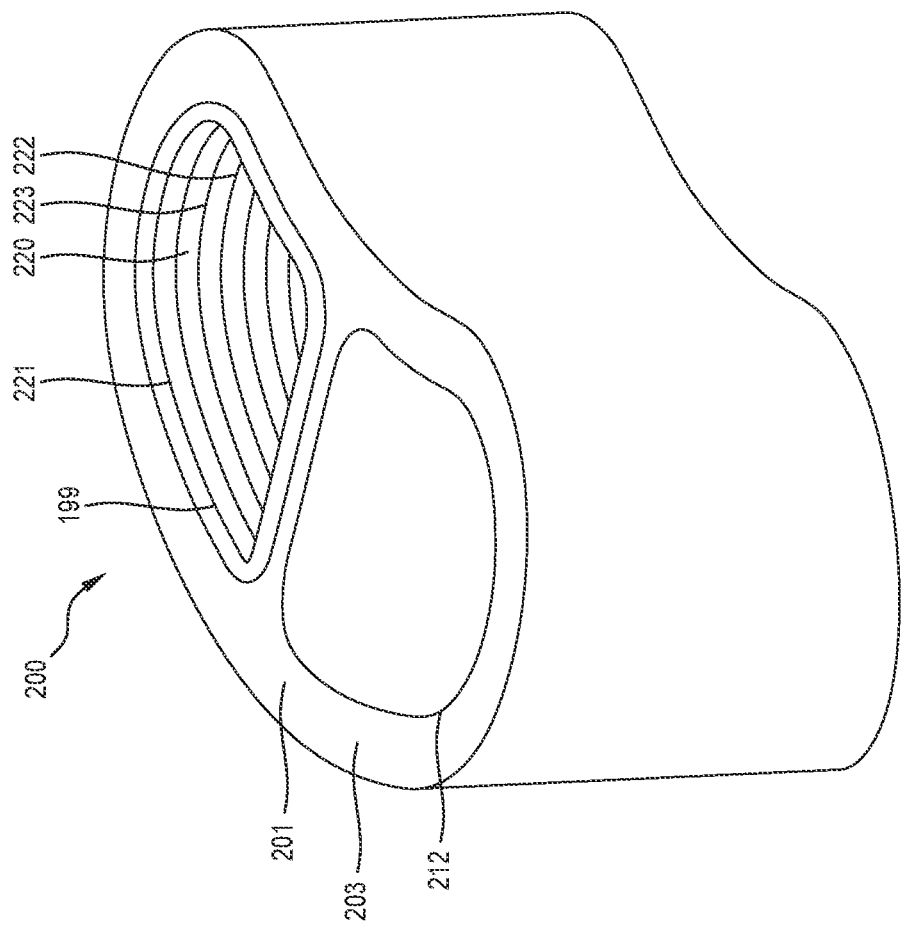
FIG. 11 provides a perspective view of a tenth embodiment of the device of the disclosure with a single insert.
Figure 12:
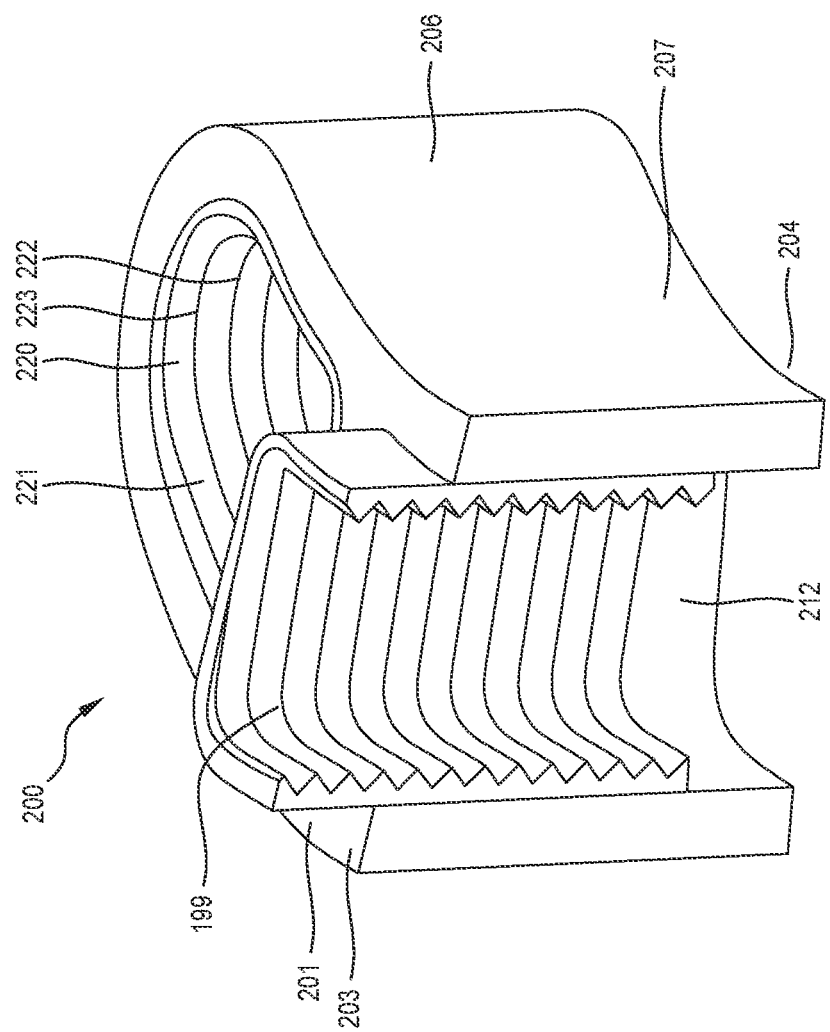
FIG. 12 provides a perspective view of the embodiment of FIG. 11 with a second insert being positioned therein.

Referring now to FIG. 10, disclosed is an interbody device 151 comprising a body 152 extending between a first end 153 and a second end 154. The body comprises walls 156 extending between the first end 153 and the second end 154.

In this illustrated embodiment the body includes an internal cavity 161 extending between the two ends. The internal cavity 161 is defined by an internal surface 162 of the body. The internal surface 162 includes a stabilising arrangement 164 in the form of an inclined surface 165 which extend inwardly from the internal surface 162.

In some forms, disclosed is an insert for an interbody device, the insert being adapted to incorporate a stabilizing assembly onto the interbody device.

Referring now to FIGS. 11-14, in one embodiment the disclosure provides an insert 199 for an interbody device 200 comprising a body 201 extending between a first end 203 and a second end 204. The body 201 is generally sized and shaped to be positioned between vertebral bodies. In this embodiment the body comprises a curved wall 206 defined by an outer surface 207 and inner surface 212 extending between the first end 203 and the second end 204. A strut 208 extends through the internal cavity to provide structural support.

In some forms the body 2 is composed of polyether ether ketone, polylactides or biocompatible polymers, carbon-fibre composites, titanium, polyethylene, silicon nitride, or allograft, xenograft, autograft or other biologically compatible materials.

In some forms the insert 199 is composed of the same material. In some forms the insert 199 and body 202 are composed of different materials In this illustrated embodiment the body includes an internal cavity 211 extending between the two ends. The internal cavity 211 is defined by the inner surface 212 of the body. The insert 199 is configured to be fit into the cavity 211 and secured therein. In some forms the insert 199 is secured by press-fit, by interference fit, by mechanical securing or by the shape of the internal cavity 211.

The insert 199 includes an inner surface 220 that includes a stabilising arrangement 221 in the form of a profile 222 which means a portion of the surface 212 extends at an angle with respect to the overall movement of the surface between the ends. This profile 222 on the surface 220 forms a laterally extending surface 223 which is configured in use to engage with the bone or connective tissues as they grow.

Figure 13:
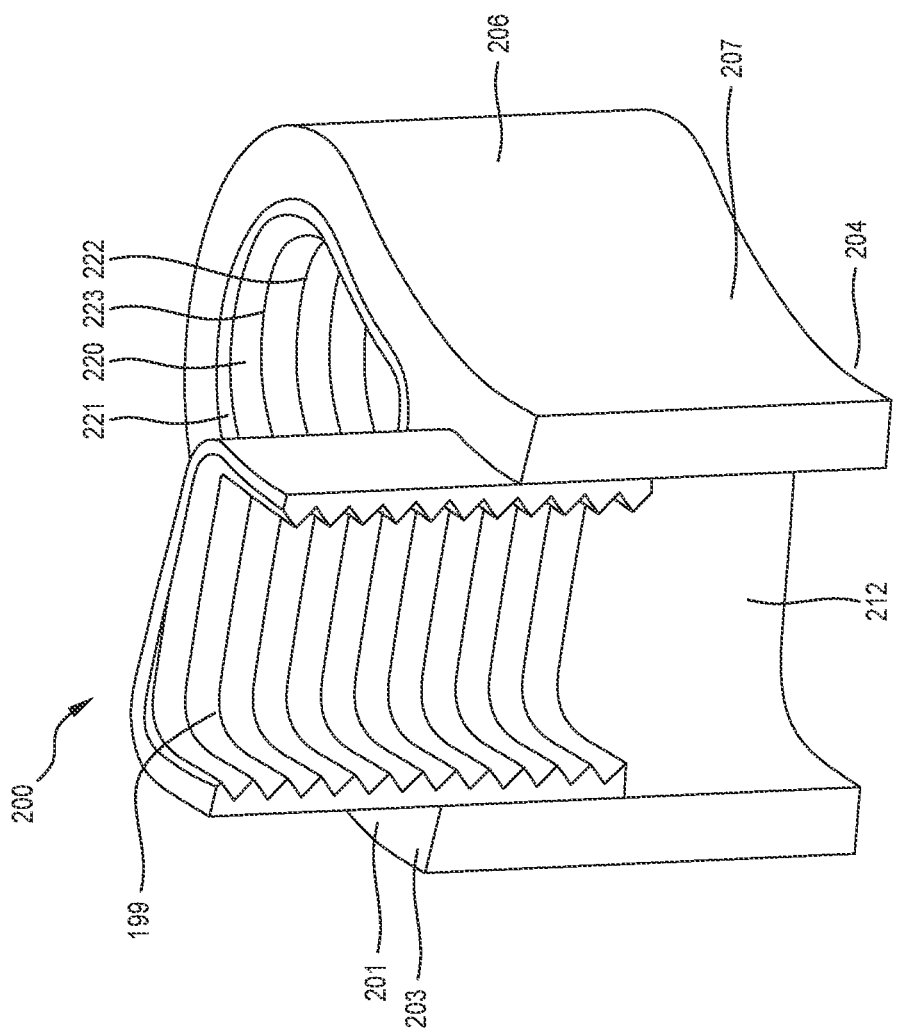
FIG. 13 provides a perspective view of the embodiment of FIG. 11 with a second insert being positioned therein.
Figure 14:
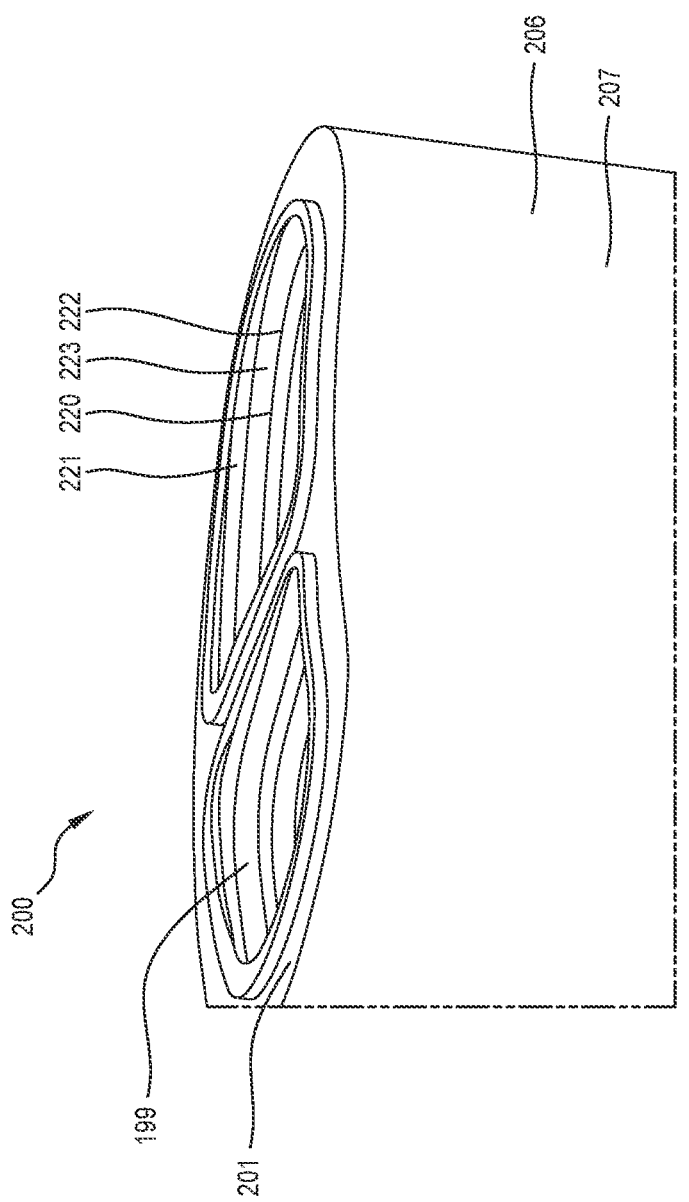
FIG. 14 provides a perspective view of the embodiment of FIG. 11, with two inserts positioned therein.
Figure 15:
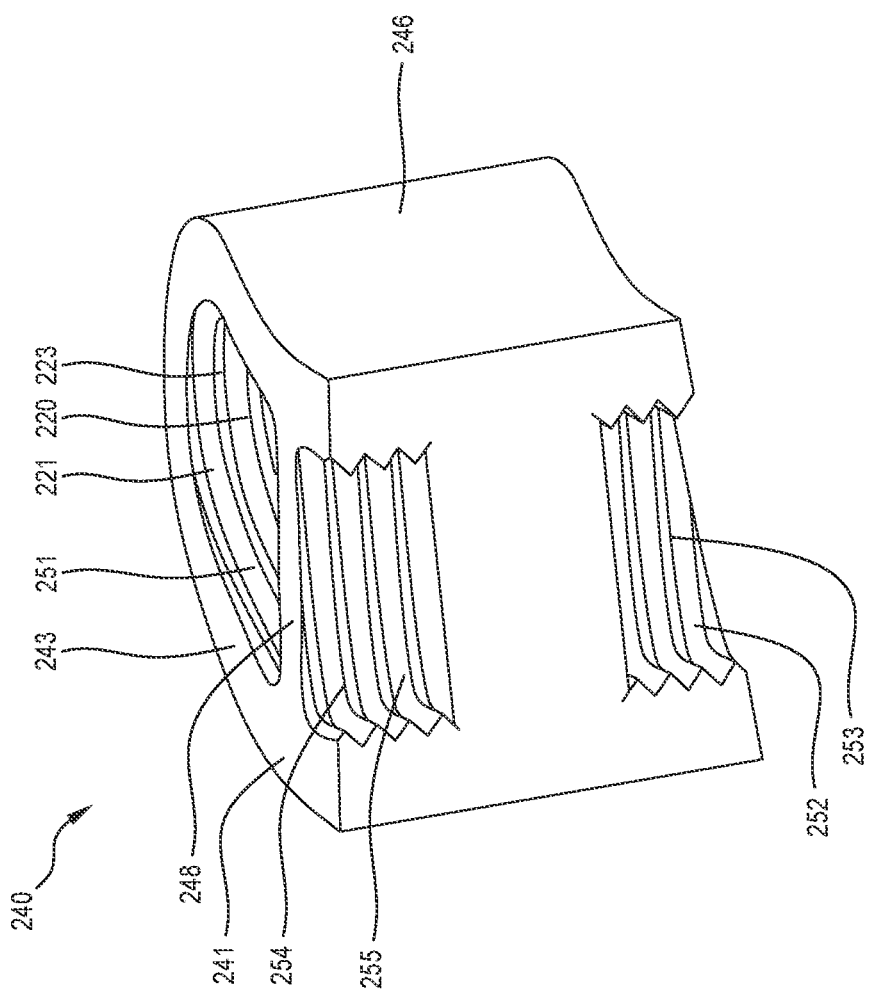
FIG. 15 provides a perspective view of an eleventh embodiment of the device of the disclosure.

The insert is positionable within the internal cavity as shown in FIGS. 13 and 14. As shown in FIG. 15 the insert 199 may protrude slightly from the internal cavity 211.

In use, an insert is selected and the interbody device is positioned between two vertebral bodies. Bone graft material is deposited (or alternatively pre-loaded) within the internal cavity 211 to support or stimulate bone growth from the vertebral bodies. In this embodiment, bone growing into the internal cavity 211 of the body 202 may grow around the profile 221 causing bone ingrowth around the laterally extending surface 223. Specifically, the bone ingrowth may occur within 10 mm or preferably within 1 to 3 mm of either end 203, 204 of the body 202 providing spinal stability prior to engagement of the bone. In some embodiments and cases bone to bone union will not be required to produce spinal stability.

Referring now to FIG. 15, disclosed is an interbody device 240 comprising a body 241 extending between a first end 243 and a second end. As in the first embodiment, in this embodiment the body comprises a curved wall 246 extending between the first end 243 and the second end 244. A strut 248 extends through the internal cavity to provide structural support.

In this illustrated embodiment the body includes an internal cavity 251 extending from a first end into the body and a separate internal cavity 252 extending from the second end into the body. The internal cavities 251 and 252 are defined by an internal surface 253 of the body. The internal surface 253 includes a stabilising arrangement 254 in the form of a profile 255 which means a portion of the surface 253 extends at an angle with respect to the overall movement of the surface between the ends.

In this form the cavity does not extend the full way through the interbody device because bone to bone union is not required. This has the benefit of allowing a surgeon to load the interbody device with different graft or materials or an antibiotic depending upon the needs of the different vertebral regions.

Figure 16:
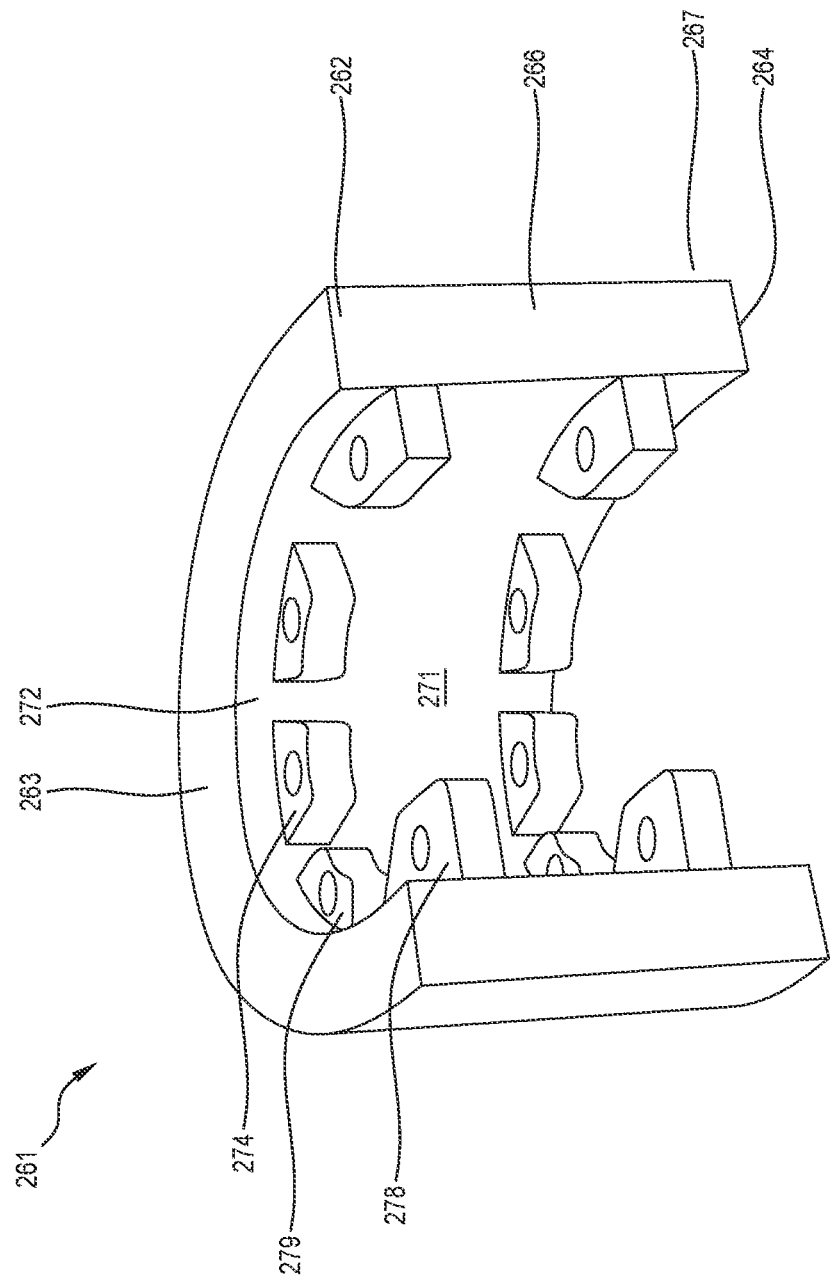
FIG. 16 provides a perspective view of a twelfth embodiment of the device of the disclosure.

Referring now to FIG. 16, in one embodiment the disclosure provides an interbody device 261 comprising a body 262 extending between a first end 263 and a second end 264. The body 262 is generally sized and shaped to be positioned between vertebral bodies. In this embodiment the body comprises a curved wall 266 defined by an outer surface 267 and inner surface 272 extending between the first end 263 and the second end 264. A strut 268 extends through the internal cavity to provide structural support.

In this illustrated embodiment the body includes an internal cavity 271 extending between the two ends. The internal cavity 271 is defined by the inner surface 272 of the body. The inner surface 272 includes a stabilising arrangement 274 in the form of a series of protrusions 278 extending inwardly from the inner surface of the cavity 271. The protrusions 278 in this embodiment are spaced apart around the diameter of the inner surface of the cavity and located proximal to an end of the device. The protrusions extend from the wall of the device and include an aperture 279 extending through the protrusion 278.

Figure 17:
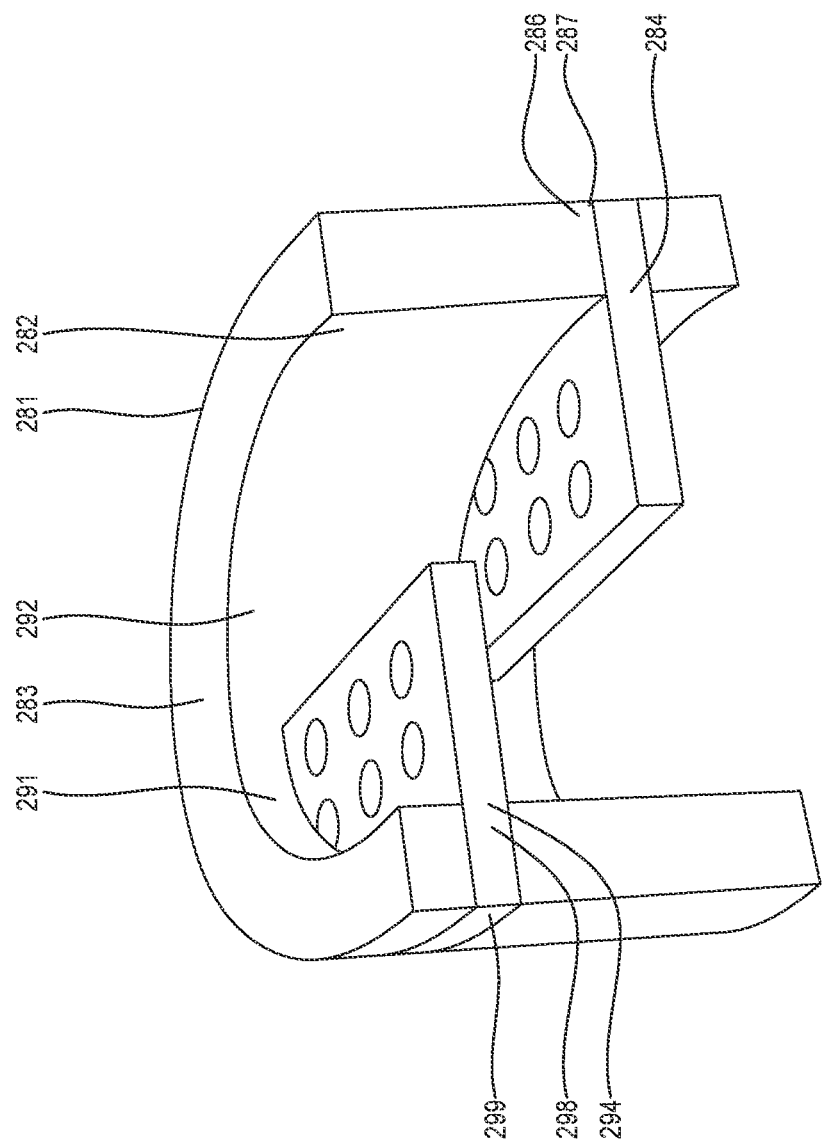
FIG. 17 provides a perspective view of a thirteenth embodiment of the device of the disclosure.

Referring now to FIG. 17, in one embodiment the disclosure provides an interbody device 281 comprising a body 282 extending between a first end 283 and a second end 284. The body 282 is generally sized and shaped to be positioned between vertebral bodies. In this embodiment the body comprises a curved wall 286 defined by an outer surface 287 and inner surface 292 extending between the first end 283 and the second end 284.

In this illustrated embodiment the body includes an internal cavity 291 extending between the two ends. The internal cavity 291 is defined by the inner surface 292 of the body. The inner surface 292 includes a stabilising arrangement 294 in the form of a plate 298 extending through a slot 299 in the inner surface 292 of the body. The plate is removably positioned within the slot. The slot 299 is sized and shaped such that the plate 298 extends therethrough and is generally retained in position. The plate 299 in this embodiment are positioned proximal to an end of the device and are generally flat. In the illustrated form the plate 299 includes apertures extending therethrough.

The insertion of the plates 298 through the slots 299 can be utilised to compress or relocate material such as bone graft loaded within the cavity. This can be utilised to increase packing and efficiency of the bone graft.

Figure 18:
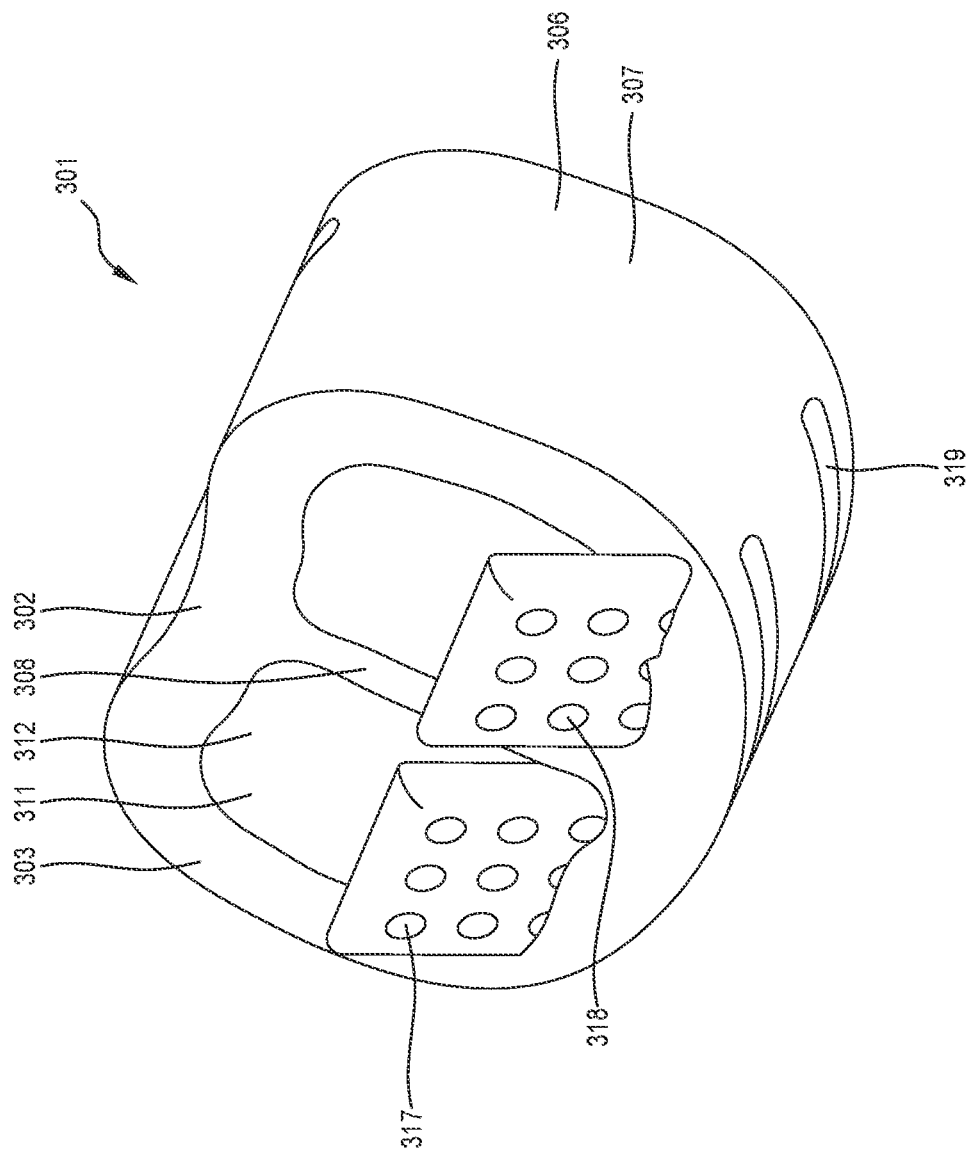
FIG. 18 provides a perspective view of a fourteenth embodiment of the device of the disclosure.
Figure 19:
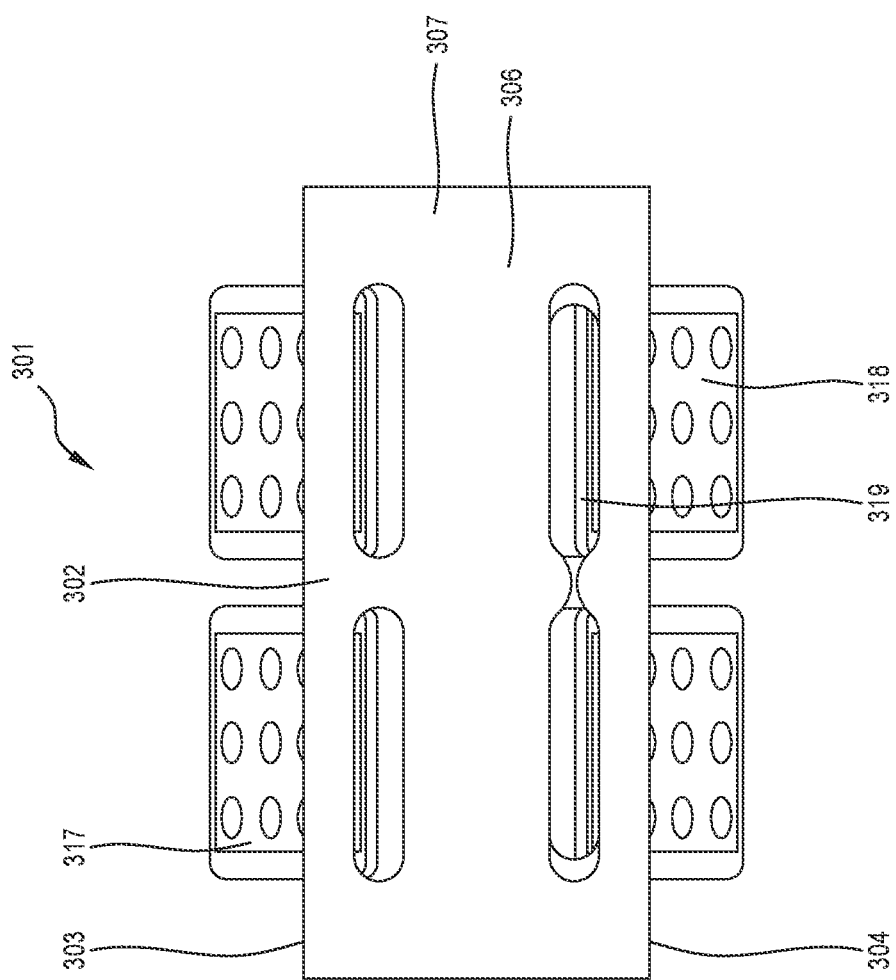
FIG. 19 provides a rear view of the device of FIG. 18.
Figure 20:
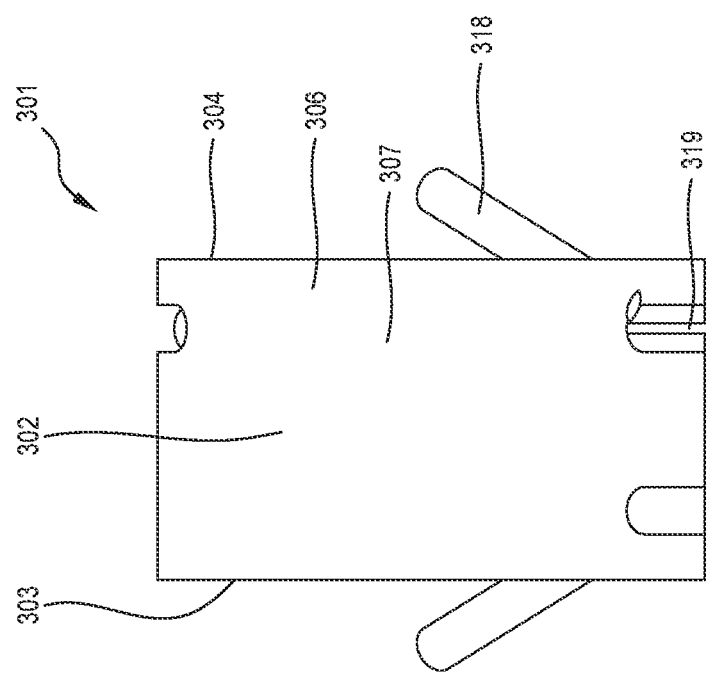
FIG. 20 provides a side view of the device of FIG. 18.

Referring now to FIGS. 18 through 20, disclosed in one embodiment is an interbody device 301 comprising a body 302 extending between a first end 303 and a second end 304. The body 302 is generally sized and shaped to be positioned between vertebral bodies. In this embodiment the body comprises a curved wall 306 defined by an outer surface 307 and inner surface 312 extending between the first end 303 and the second end 304. A strut 308 extends through the internal cavity 311 to provide structural support.

In this illustrated embodiment the body includes an internal cavity 311 extending between the two ends. The internal cavity 311 is defined by the inner surface 312 of the body. The inner surface 312 includes a stabilising arrangement in the form of a slot 319 extending through the wall of the body from the inner surface 312 of the body to the outer surface 307. A plate 318 is removably positioned through the slot. The slot 319 is sized and shaped such that the plate 318 extends therethrough and is generally retained in position. The plate 318 in this embodiment is positioned such that it can extend at an angle to the lateral. In the illustrated form it extends upwardly out of the first end 303 of the body 302. In use this has the benefit of allowing the plate 318 to enter the endplate of the vertebral body, aiding in immediate anchoring of the device to the vertebra. The device provides integration and load sharing. In the illustrated form the plate 318 includes apertures 317 extending therethrough.

Figure 21:
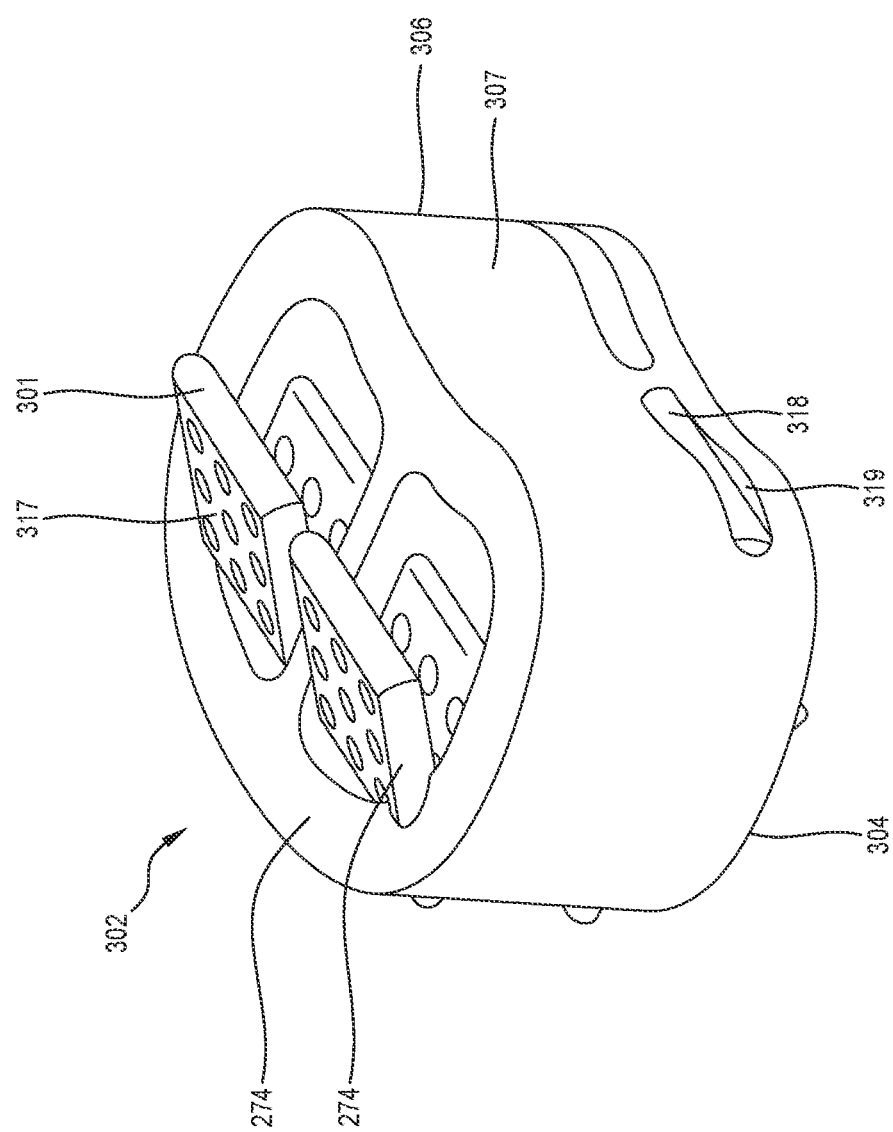
FIG. 21 provides a perspective view of a fifteenth embodiment of the device of the disclosure.
Figure 22:
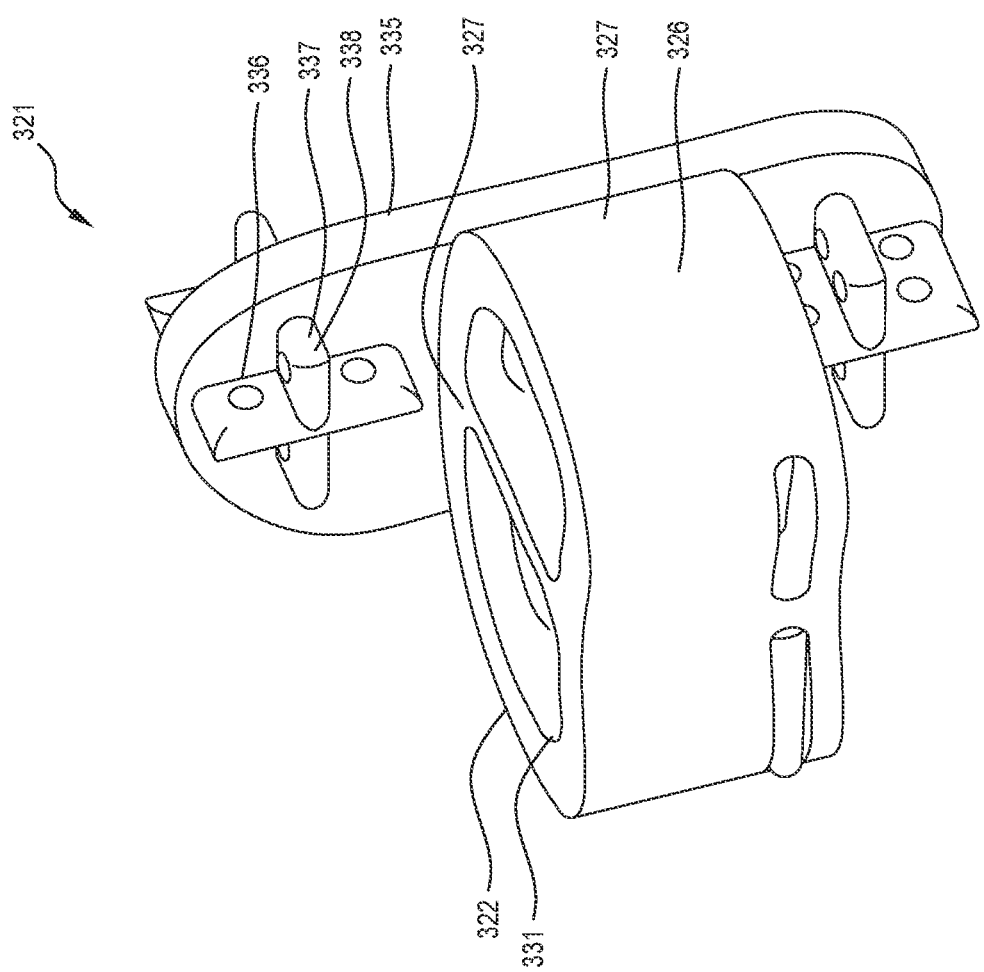
FIG. 22 provides a perspective view of a sixteenth embodiment of the device of the disclosure.
Figure 23:
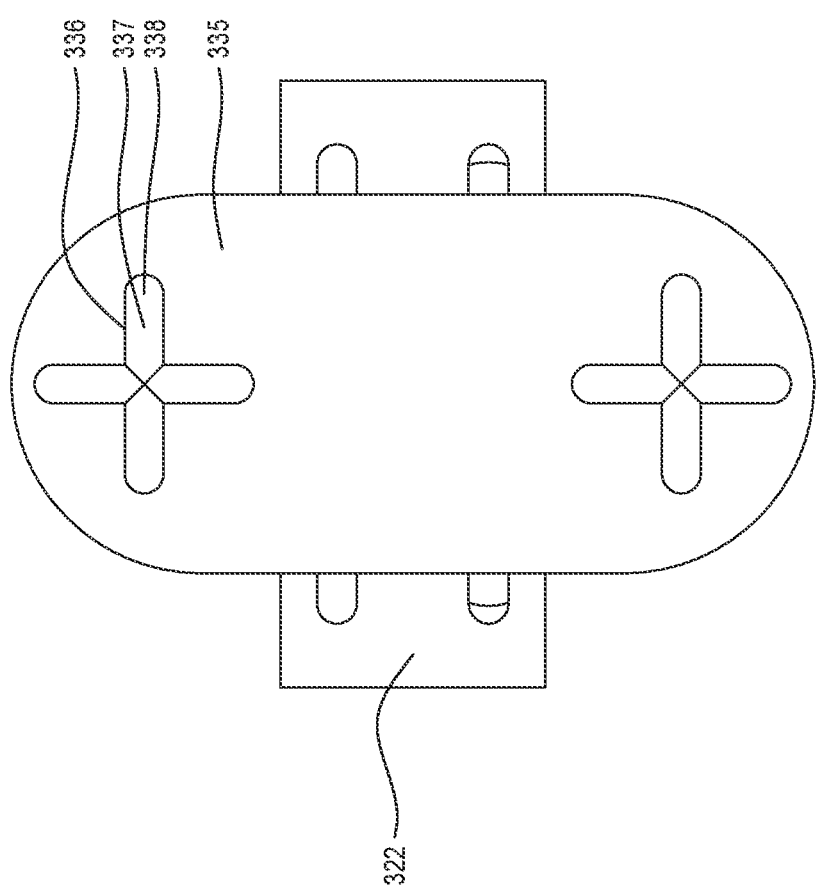
FIG. 23 provides a rear view of the device of FIG. 22.
Figure 24:
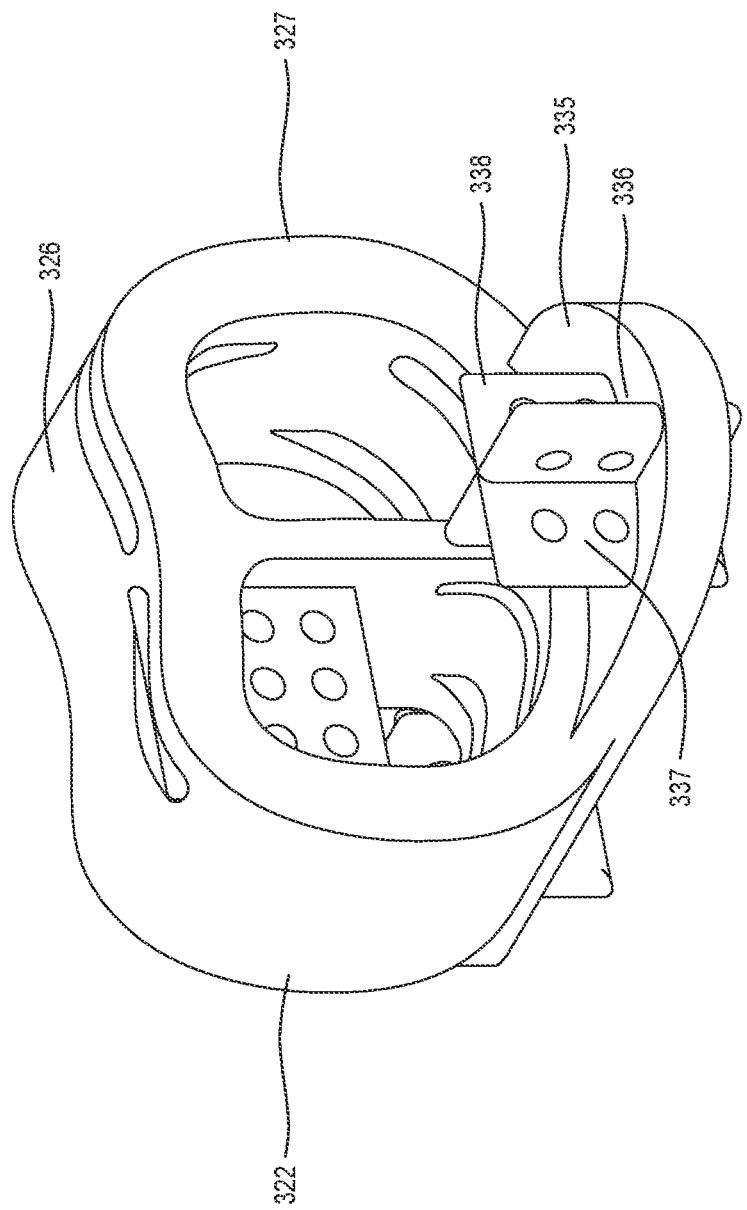
FIG. 24 provides a top perspective view of the device of FIG. 22.
Figure 25:
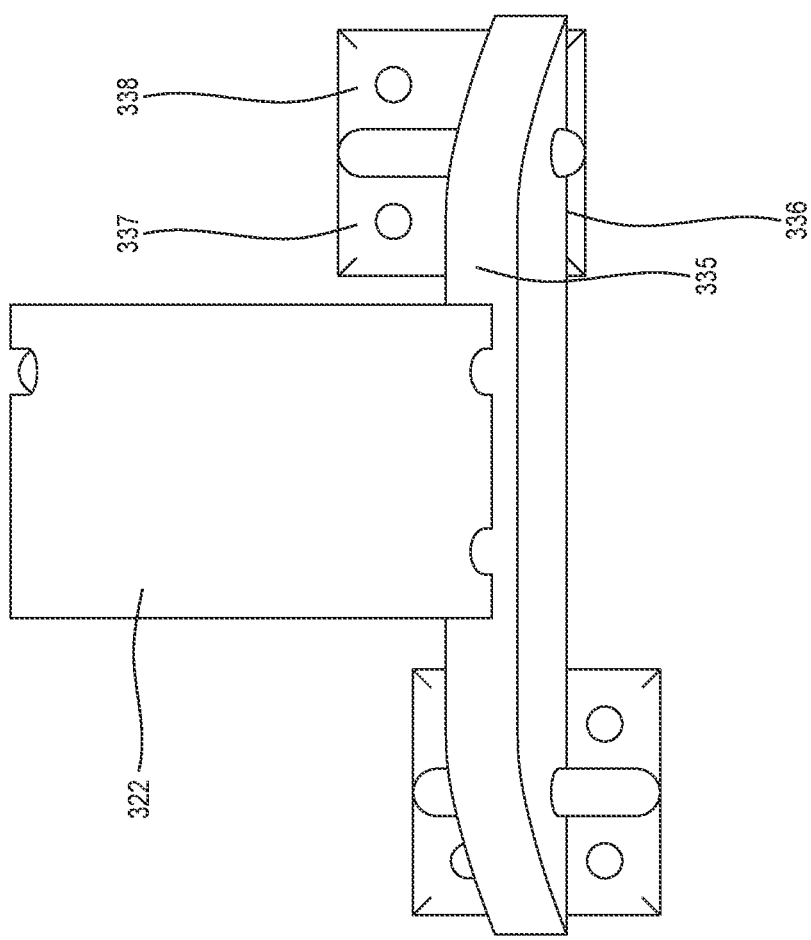
FIG. 25 provides a side view of the device of FIG. 22.
Figure 26:
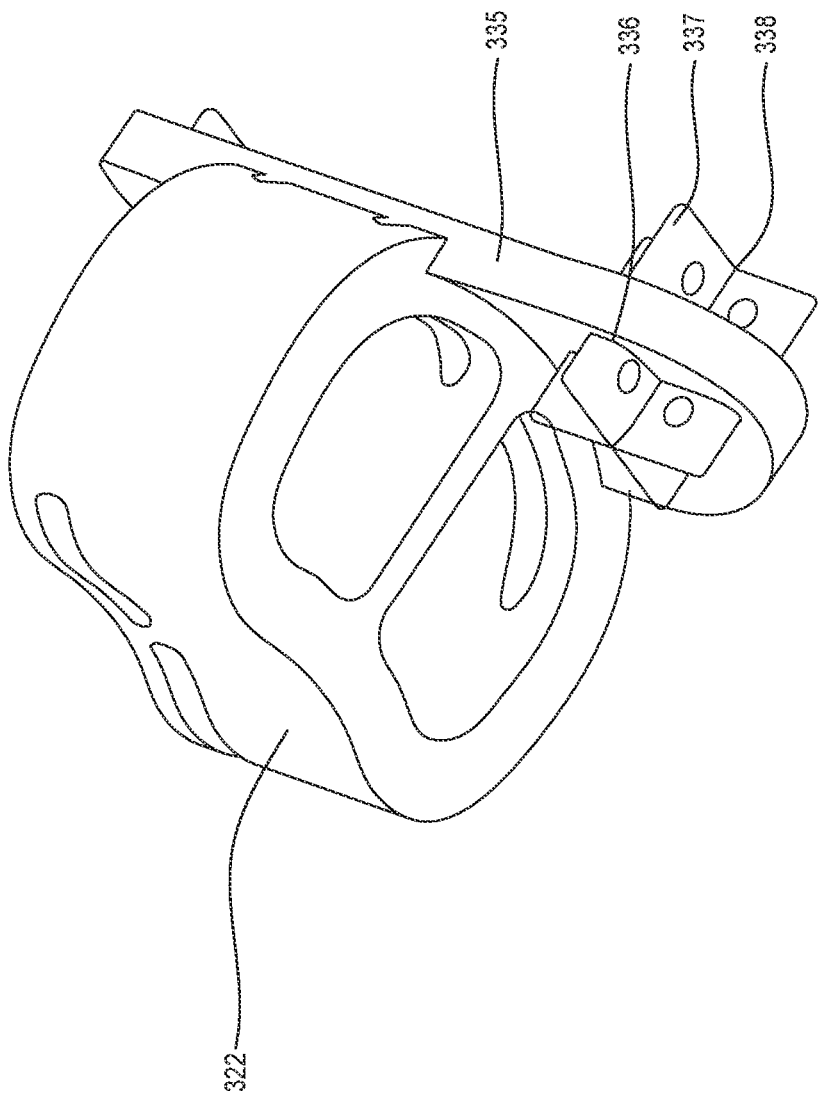
FIG. 26 provides a bottom perspective view of the device of FIG. 22.

Referring now to FIG. 21, in some forms a plurality of plates 318 can be positioned to extend through the wall of the body 302. Alternatively a plurality of angled spines or wires can extend through at different angles and different positions to allow for best anchoring.

Referring now to FIGS. 22 through 26, in one embodiment the device 321 comprises a device body 322 defined by a curved wall 326 and having an internal cavity 331 extending longitudinally therethrough.

In this form the device further comprises an anterior plate 335 which is engaged with the device body 322. The anterior plate 335 is engaged with the body 322 and extends longitudinally beyond the rear wall 327 of the body 322. The anterior plate 335 includes a plurality of slits 336 through which an anchoring member 337 can extend. In the illustrated form the anchoring member is in the form of crossed plates 338 extending longitudinally and laterally through the anterior plate. The crossed plates 338 are adapted to permit anchoring with the vertebra and to encourage ingrowth.

In other alternative embodiments, the anterior plate includes alternative anchoring members such as plates, rods, hooks, ridges or other anchoring members.

In some of the forms disclosed above, the body includes a cavity to allow for loading with material such as bone graft, antibiotic or other beneficial materials.

In some forms the stabilising arrangements may be added during or immediately prior to surgery by providing a device with no stabilising features and a kit to allow a surgeon to incorporate the most suitable profile or projection or depression on the device.

Referring now to FIGS. 27A through 27D, prior art interbody devices 350 are shown positioned between vertebrae 351 and 352. The interbody device comprises a wall 355 defining an interior cavity 356. In use bone graft 358 is positioned within the cavity to encourage bone growth through the cavity. In most cases spinal stability is achieved when the bone growing from vertebra 351 reaches that growing from vertebra 352.

Referring to FIGS. 28A through 28D, in one embodiment of the disclosure the present device comprises a body 360 positioned between vertebrae 361 and 362. The body 360 comprises a wall 365 defining an internal cavity 366. The body 360 includes stabilising arrangements 367 in the form or a plurality of protrusions 368 having apertures 369 extending therethrough. The protrusions in this form extend inwardly from the wall 365 into the internal cavity 366 and are generally of a rounded polygonal shape. In use bone graft 364 can be located within the internal cavity 366 to encourage bone growth. The graft 364 can be generally located about the protrusions.

Referring to FIGS. 29A through 29D, in one embodiment of the disclosure the present device comprises a body 370 positioned between vertebrae 371 and 372. The body 370 comprises a wall 375 defining an internal cavity 376. The body 370 includes stabilising arrangements 377 in the form of plates extending from the wall 375 into the internal cavity 376. In his form the plates are essentially flat and include apertures 379 extending therethrough. In some forms the plates are removably inserted into slots in the wall. In use bone graft 374 can be located within the internal cavity 376 to encourage bone growth. The graft 374 can be generally located about the plates 377.

Referring to FIGS. 30A through 30D, in one embodiment of the disclosure the present device comprises a body 380 positioned between vertebrae 381 and 382. The body 380 comprises a wall 385 defining an internal cavity 386. The body 380 includes stabilising arrangements 387 in the form of plates extending from the wall 385 into the internal cavity 386. In his form the plates are essentially flat and include apertures 389 extending therethrough. In some forms the plates are removably inserted into slots in the wall. In use bone graft 384 can be located within the internal cavity 386 to encourage bone growth. The graft 384 can be located all the way through the internal cavity 386

In these embodiments shown, spinal stability may be gained when the bone grown into the internal cavity and engages a stabilising arrangement. Spinal stability may occur when stabilising arrangements positioned at the top and the bottom of the device body are engaged.

Figure 31:
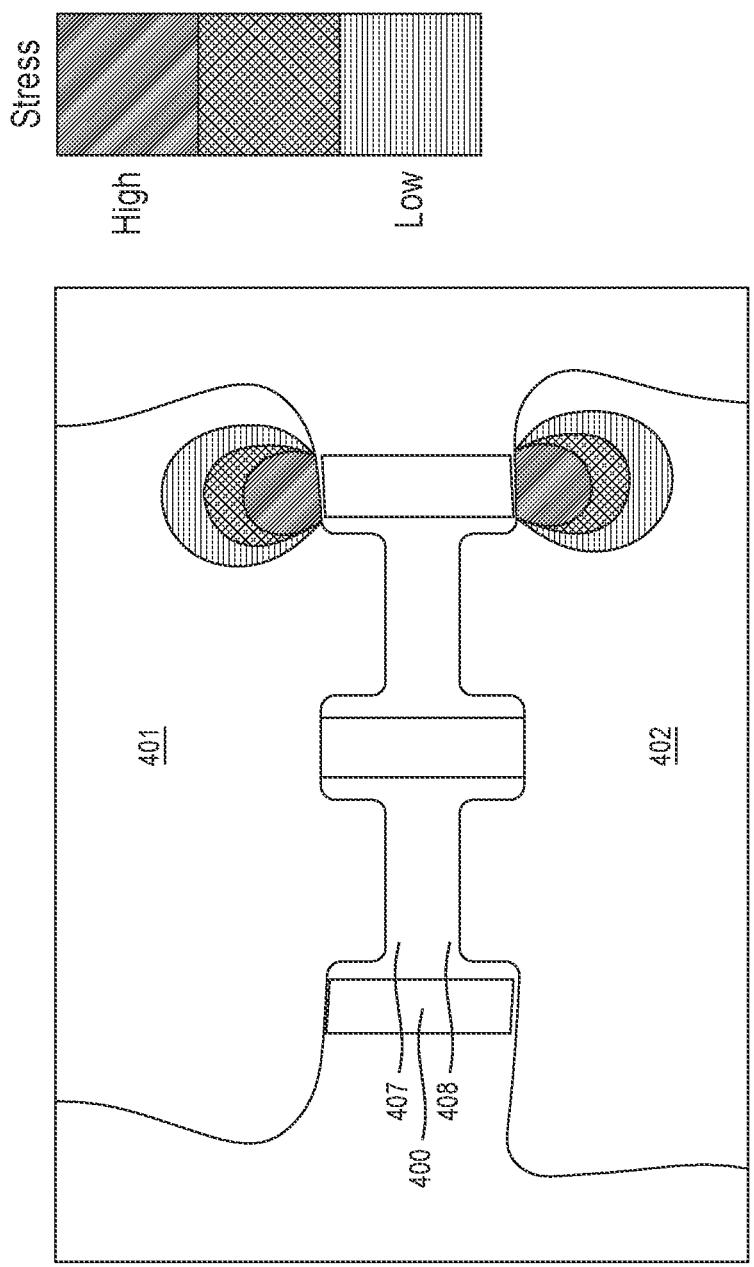
FIG. 31 provides a cross sectional view of a prior art device in use, showing stress on the vertebrae.

Referring now to FIG. 31, an interbody device 400 of the prior art is shown in position between vertebrae 401 and 402. In the illustration, there has been bone growth 403 from the vertebrae into the internal cavity 407 of the device 400. The bone growth has not engaged with bone growth from the respective vertebra. There is therefore a space 408 between the bone.

Stress on the vertebra is shown under a bending load, with the bottom vertebra anchored and the top vertebra experiencing a clockwise bending moment, highest stress occurs closest to the meeting between the interbody device and the vertebra.

Figure 32:
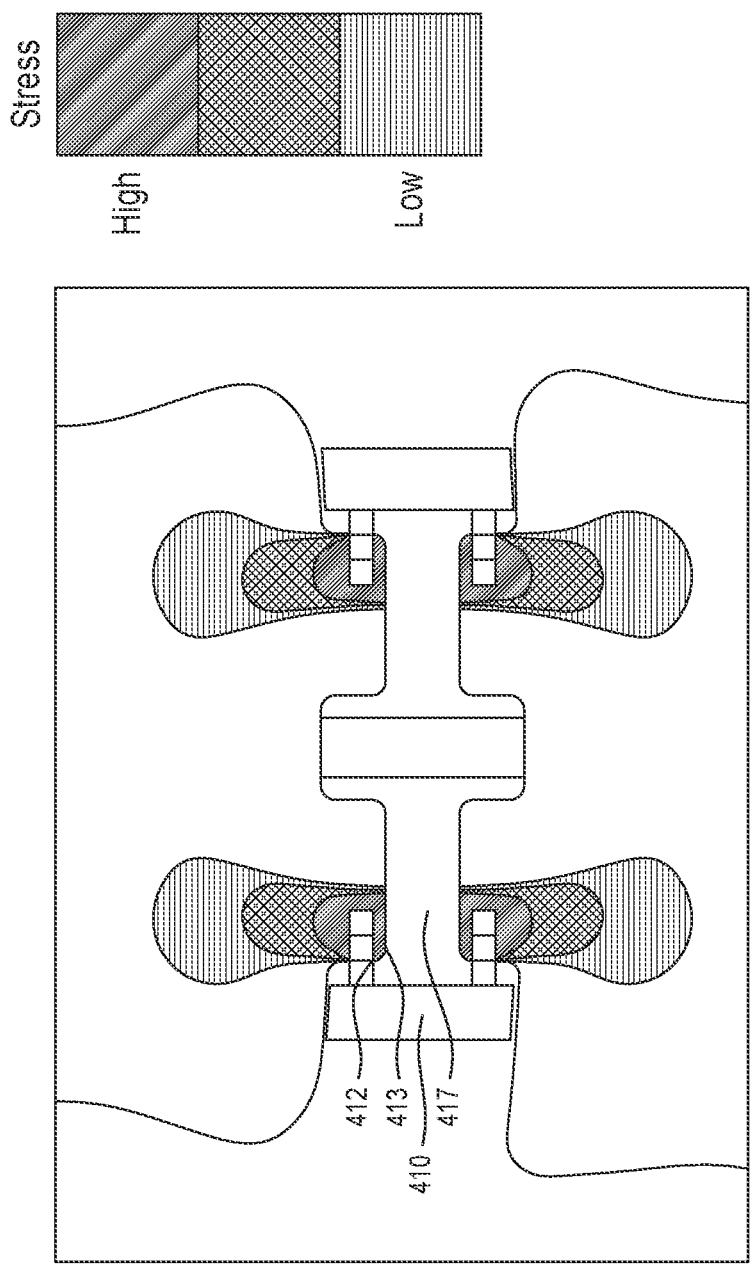
FIG. 32 provides a cross sectional view of a device of one embodiment of the disclosure in use, showing stress on the vertebrae.

In FIG. 32, the device 410 is one disclosed in the present disclosure and includes internal stabilising arrangements 412 extending into the internal cavity 417. The bone growth 413 has engaged the stabilising arrangements 412. Load transfer from the engagement features, through the graft and to the vertebra is evident.

Figure 33:
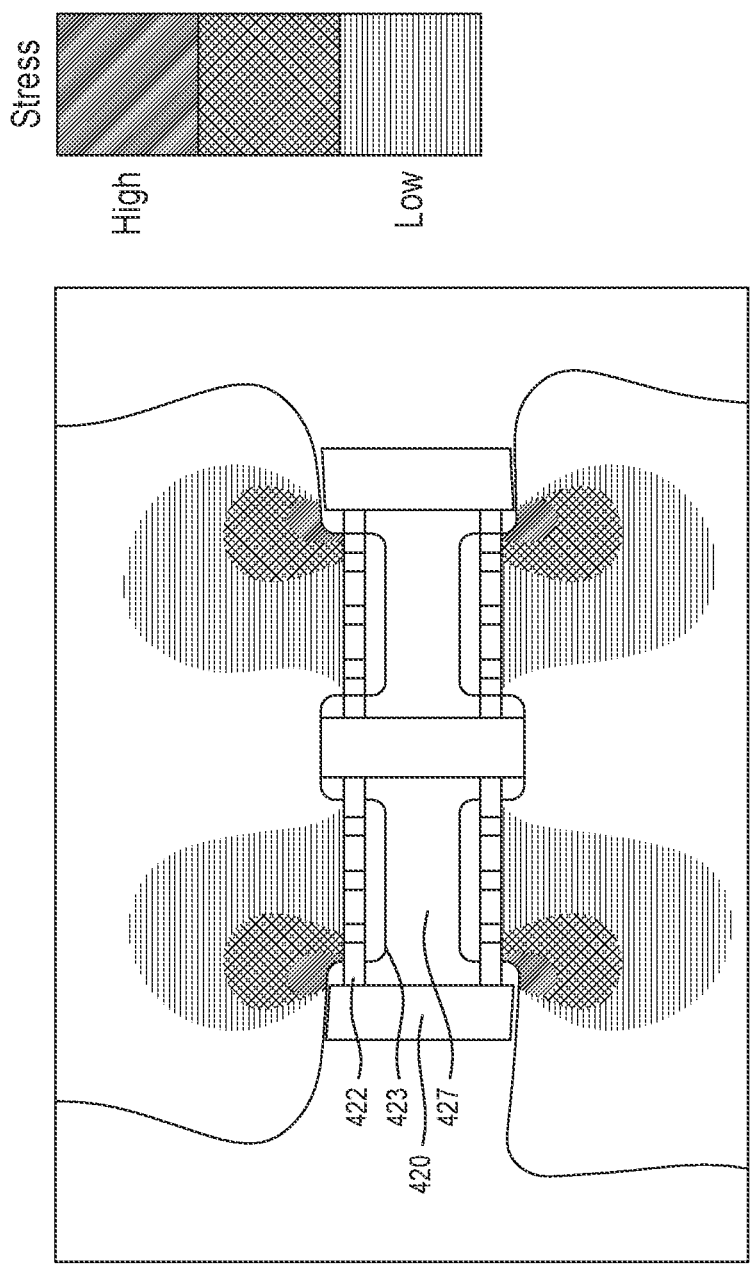
FIG. 33 provides a cross sectional view of a device of one embodiment of the disclosure in use, showing stress on the vertebrae.

In FIG. 33, the device 420 is one disclosed in the present disclosure and includes internal stabilising arrangements 422 extending into the internal cavity 427. The bone growth 423 has engaged the stabilising arrangements 422. Load transfer from the engagement features, through the graft and to the vertebra is evident.

In a further embodiment, the device comprises a body having an internal cavity extending therethrough. In this device the cavity is defined by an outer wall which may be curved or planar and extends longitudinally to define the cavity. The cavity is also generally closed at top and bottom. The top and bottom surfaces include a plurality of apertures extending therethrough. These apertures allow bone growth through the device. The bone growth then engages the top or bottom surface mechanically. In this form the top and bottom closed surfaces act as the stabilising arrangements.

In some forms this embodiment may include a side aperture to allow graft to be positioned within the device during surgery.

It will be clear to a person skilled in the art that there are other embodiments that will fall under the disclosure. In some not illustrated forms, the stabilising arrangement can comprise a series of wires or prongs extending through the device, through the internal cavity of the device and out. In other forms, channels can extend through the device from either end and into the internal cavity. The channels may, in some forms, be bisected by wires extending longitudinally through the device.

In other forms the strut may extend at any angle through the internal cavity. In some forms the strut may be lateral, in other forms it may be longitudinal and have a facing surface facing rearwardly in use.

Computational Modelling

Computational modelling of the device was performed. The results are shown in FIGS. 34-58.

Figure 34:
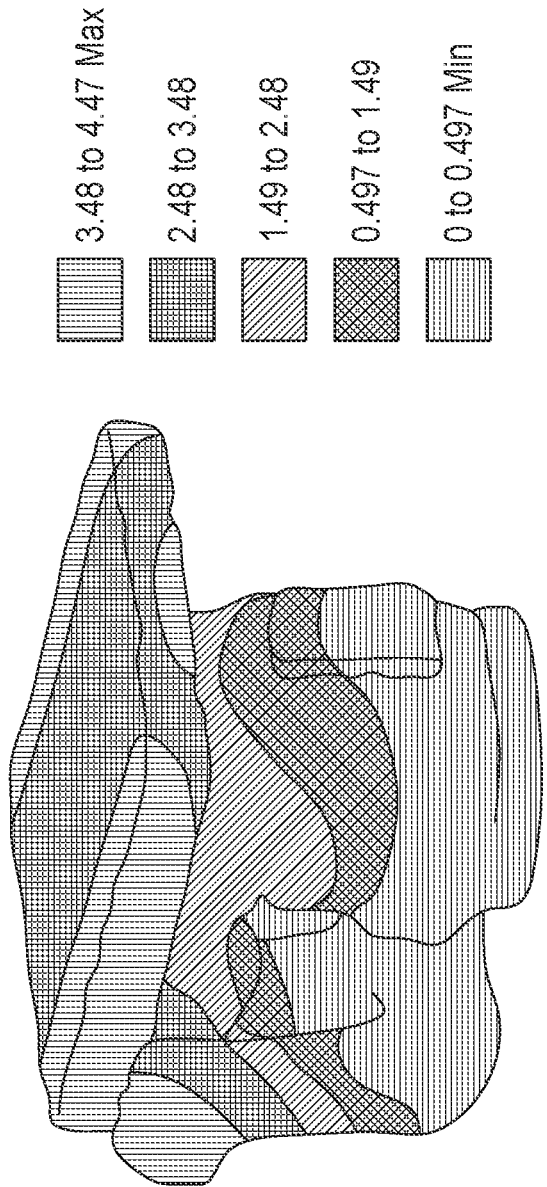
FIG. 34 shows the results of computational modeling for intact spine under global deflection in isometric view.

FIG. 34 shows results for intact spine under global deflection in isometric view in mm.

Figure 35:
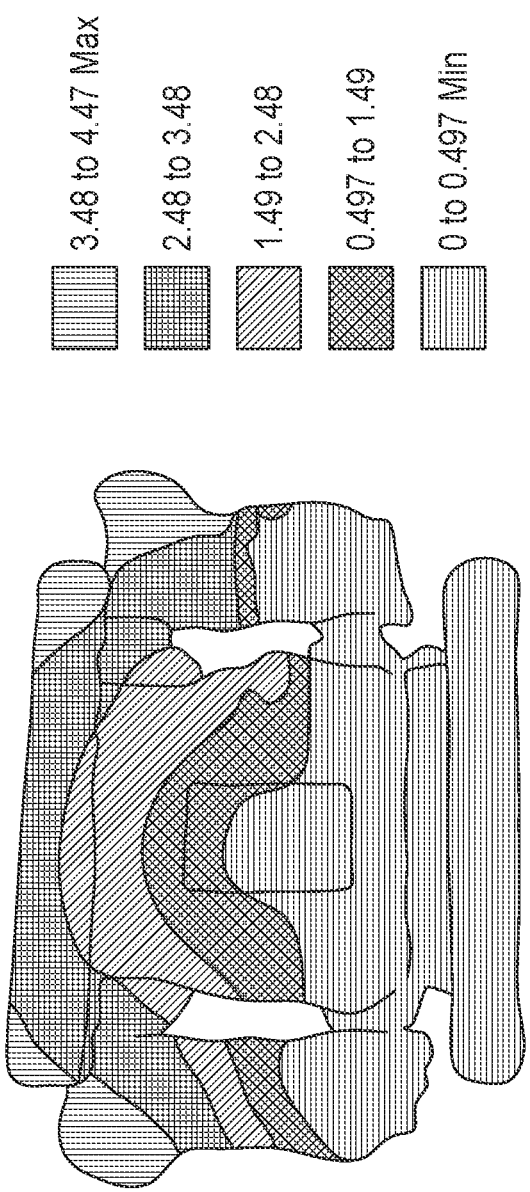
FIG. 35 shows the results of computational modeling for intact spine under global deflection in anterior view.

FIG. 35 shows the results of computational modeling for intact spine under global deflection in anterior view in mm.

Figure 36:
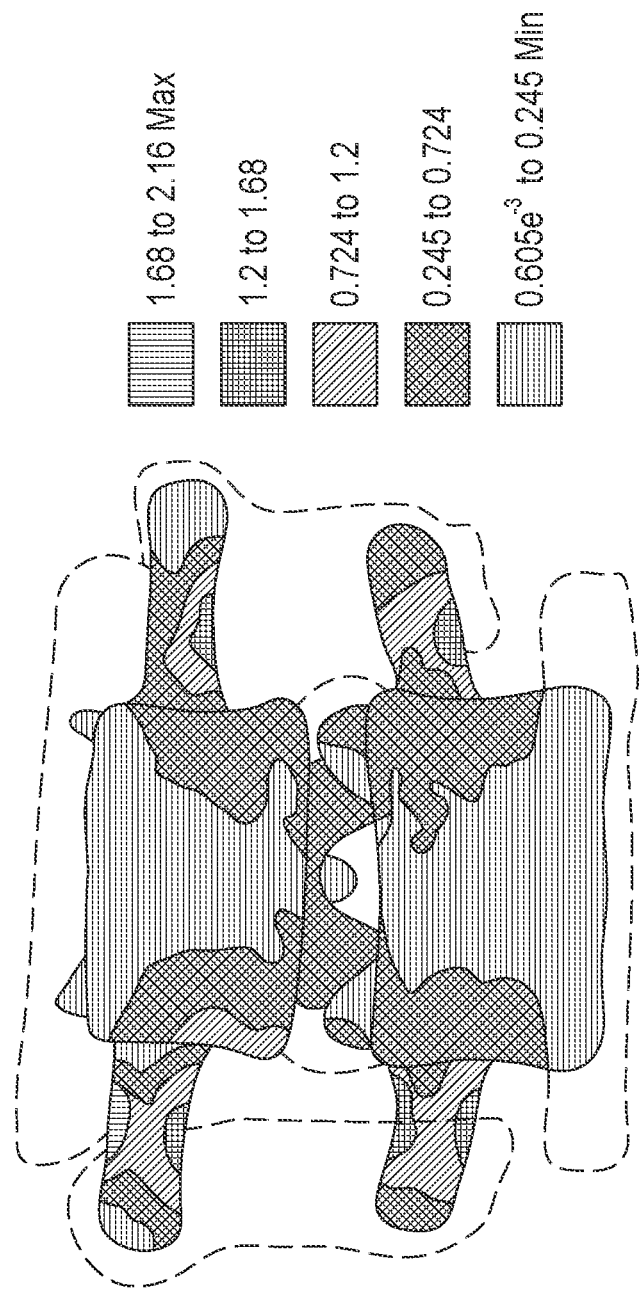
FIG. 36 shows the results of computational modeling for intact spine under von Mises stress.

FIG. 36 shows the results of computational modeling for intact spine under von Mises stress in MPa.

Figure 37:
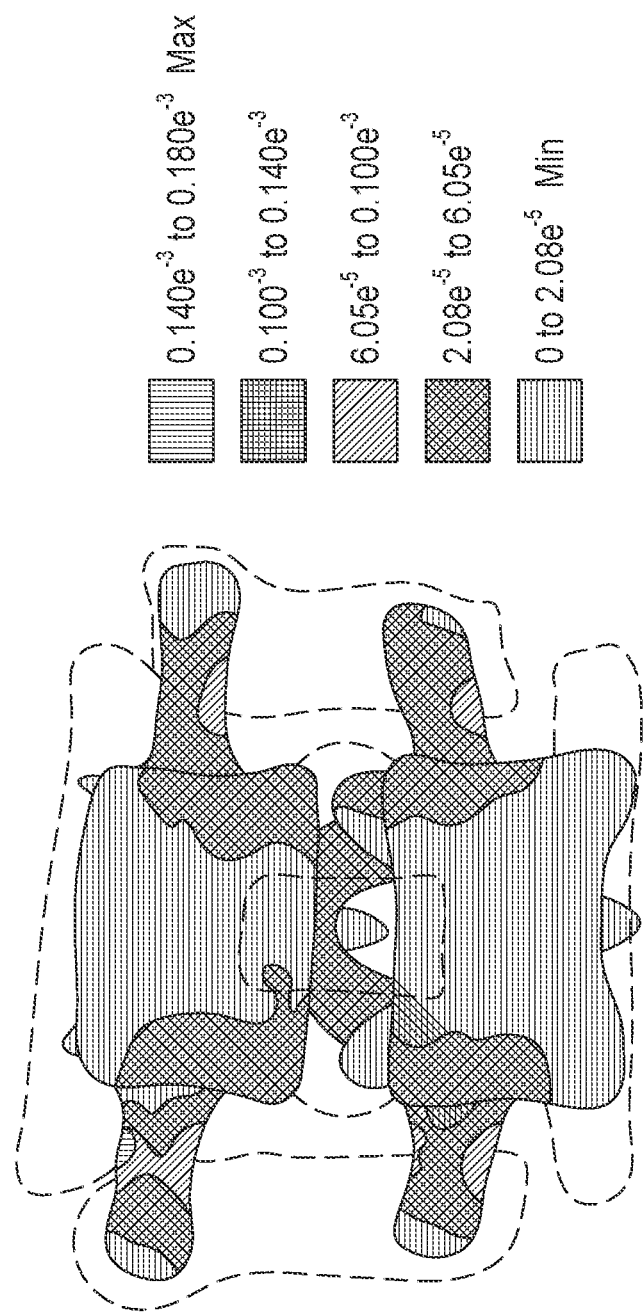
FIG. 37 shows the results of computational modeling for intact spine under von Mises strain.

FIG. 37 shows the results of computational modeling for intact spine under von Mises strain, equivalent elastic strain (mm/mm).

Figure 38:
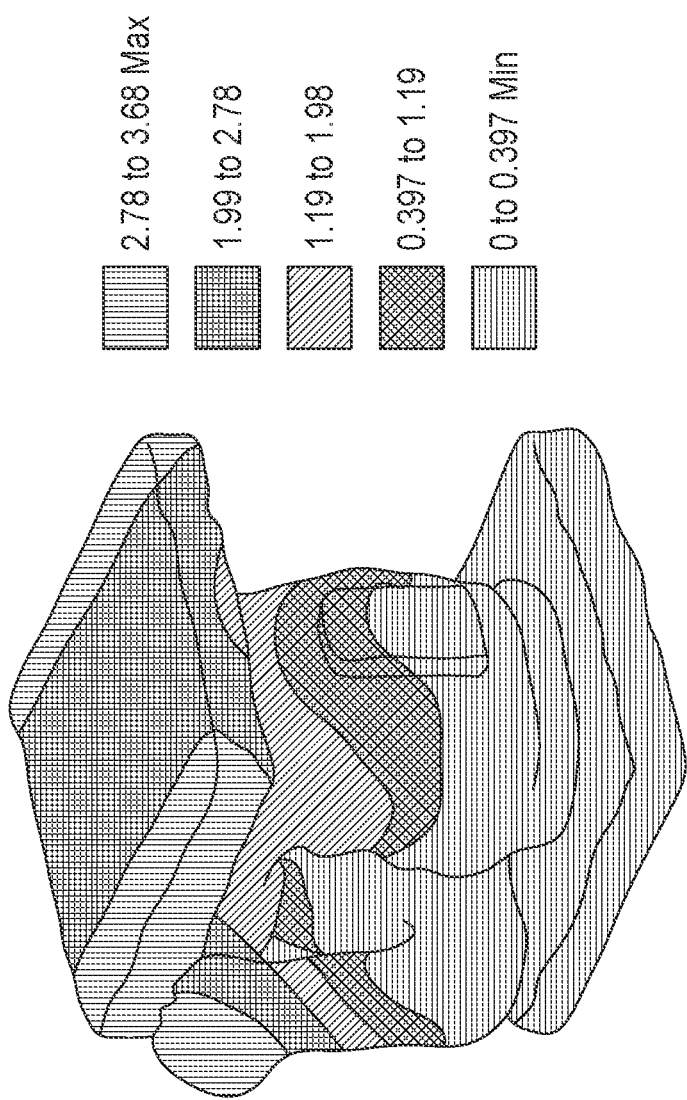
FIG. 38 shows the results of computational modeling for conventional plastic interbody device under global deflection in an isometric view.

FIG. 38 shows the results of computational modeling for conventional plastic interbody device under global deflection in an isometric view, for conventional plastic and total deformation (mm).

FIG. 39 shows the results of computational modeling for conventional plastic interbody device under global deflection in an anterior view, for conventional plastic and total deformation (mm).

Figure 40:
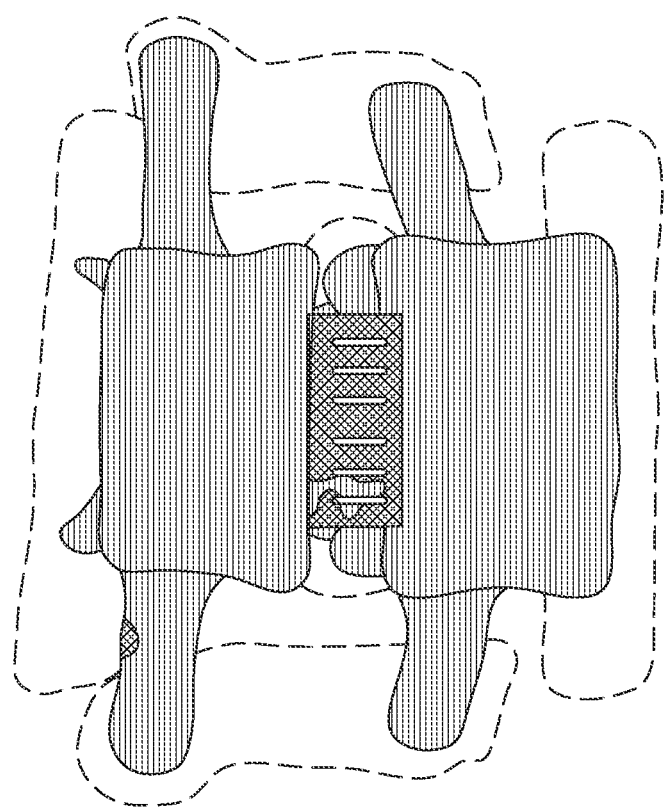
FIG. 40 shows the results of computational modeling for conventional plastic interbody device under von Mises stress in an anterior view of cage graft and bone.

FIG. 40 shows the results of computational modeling for conventional plastic interbody device under von Mises stress in an anterior view of cage graft and bone, for conventional plastic and equivalent Von Mises Stress (MPa).

Figure 41:
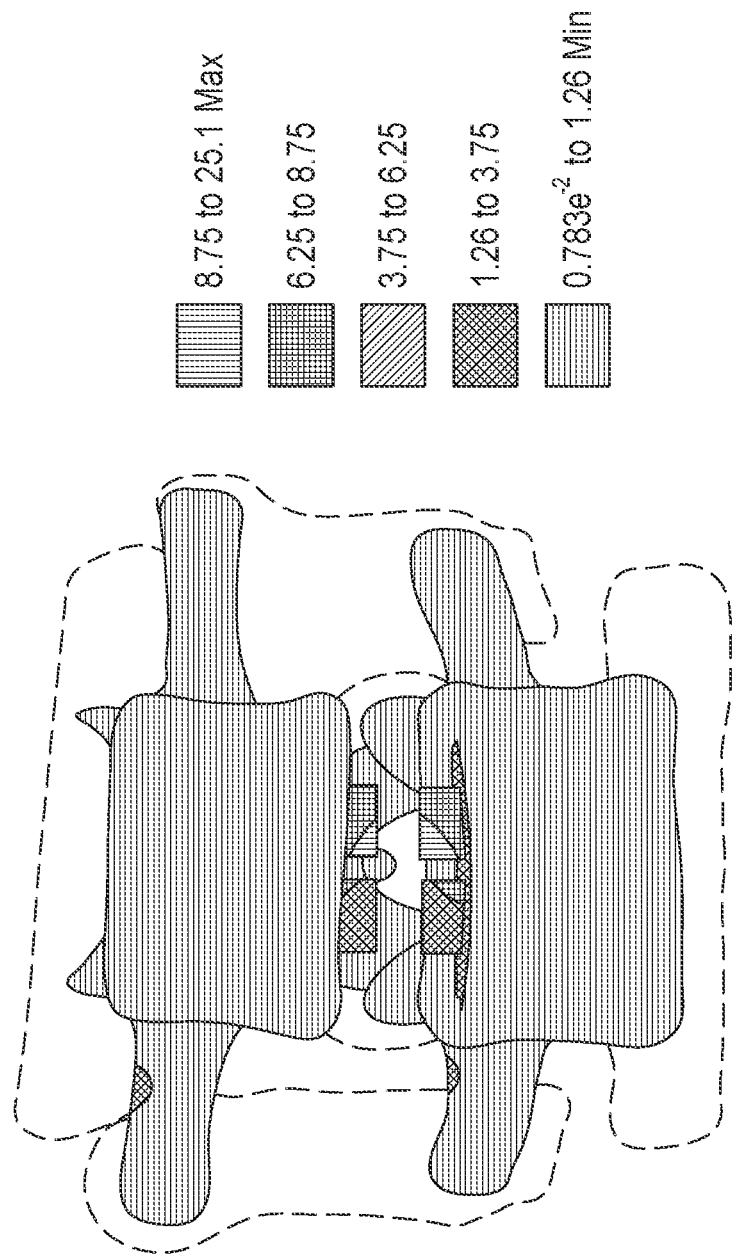
FIG. 41 shows the results of computational modeling for conventional plastic interbody device under von Mises stress in an anterior view of graft and bone.

FIG. 41 shows the results of computational modeling for conventional plastic interbody device under von Mises stress in an anterior view of graft and bone, for conventional plastic and equivalent Von Mises Stress (MPa).

Figure 42:
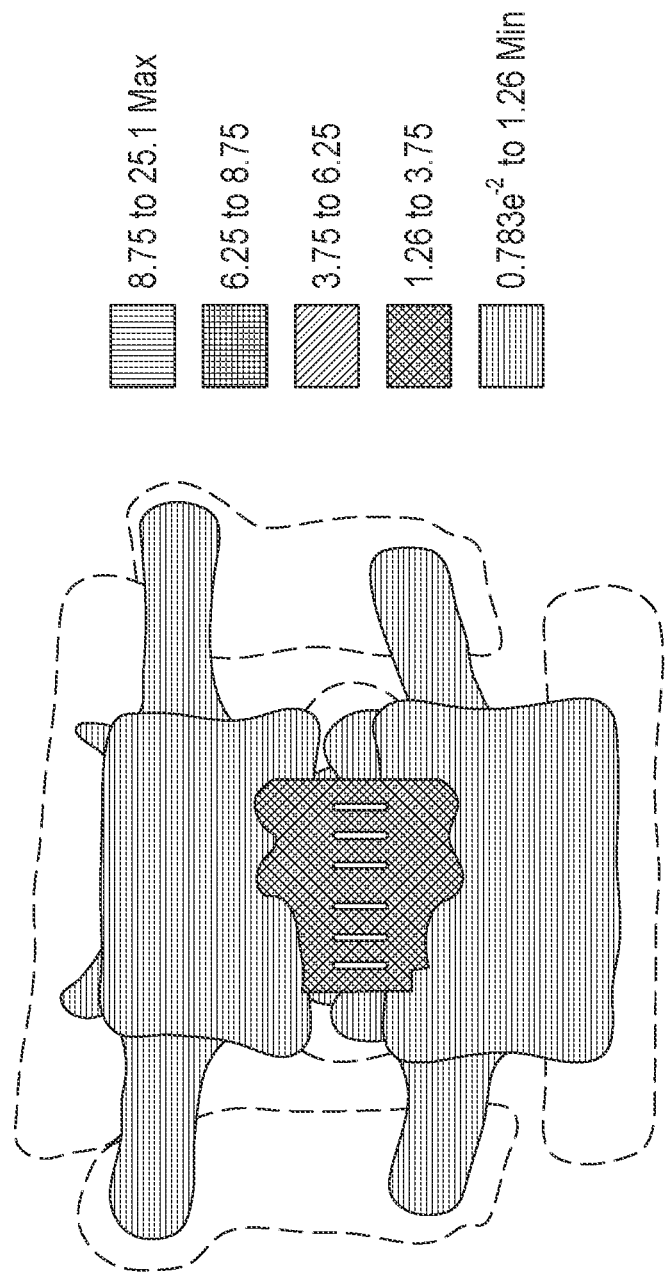
FIG. 42 shows the results of computational modeling for conventional plastic interbody device under von Mises strain in a cross sectional view of the bone graft and cage.

FIG. 42 shows the results of computational modeling for conventional plastic interbody device under von Mises strain in a cross sectional view of the bone graft and cage, for conventional plastic and equivalent Von Mises Stress (MPa).

Figure 43:
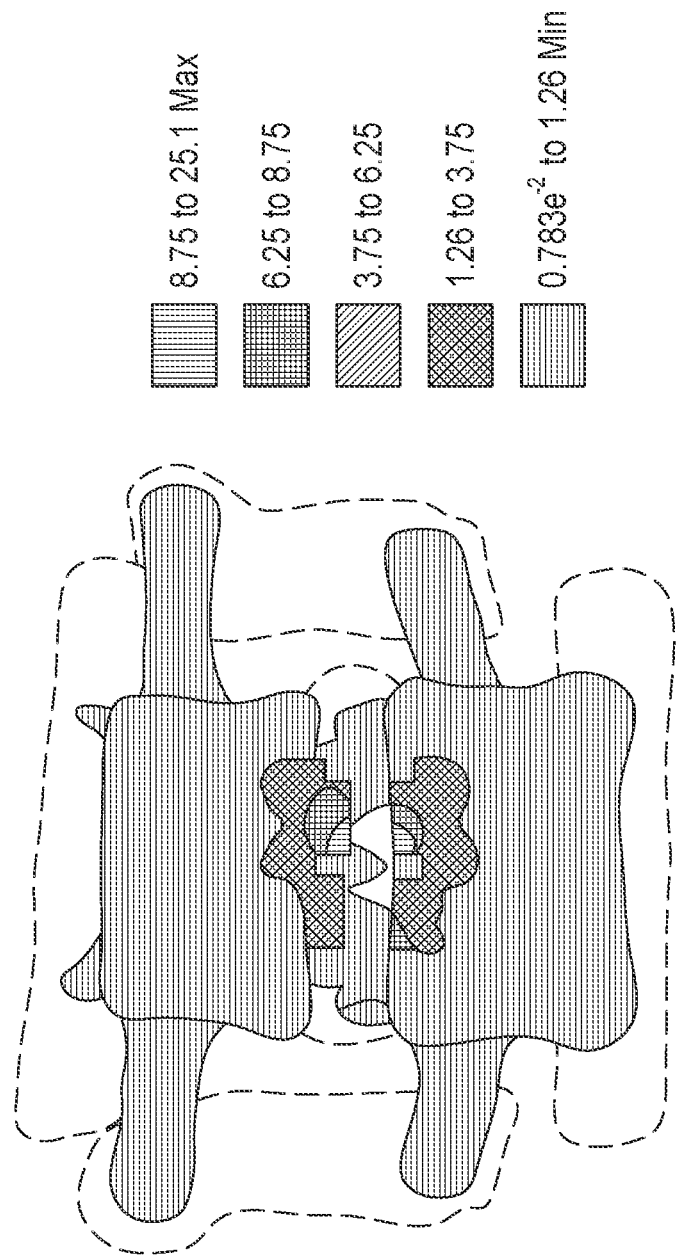
FIG. 43 shows the results of computational modeling for conventional plastic interbody device under von Mises strain in a cross sectional view of the bone and graft.

FIG. 43 shows the results of computational modeling for conventional plastic interbody device under von Mises strain in a cross sectional view of the bone and graft, for conventional plastic and equivalent Von Mises Stress (MPa).

Figure 44:
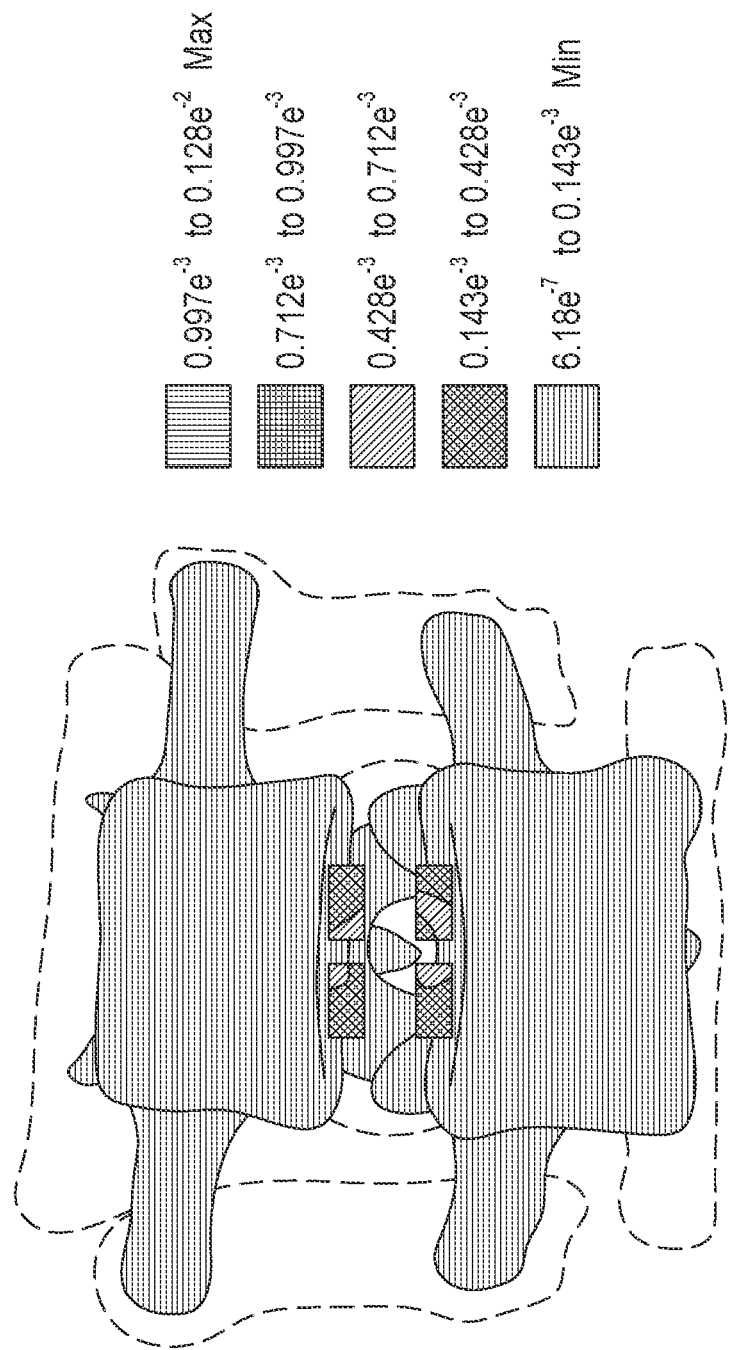
FIG. 44 shows the results of computational modeling for conventional plastic interbody device under von Mises strain in a cross sectional view of the graft and cage.

FIG. 44 shows the results of computational modeling for conventional plastic interbody device under von Mises strain in a cross sectional view of the graft and cage, for conventional plastic and equivalent elastic strain (mm/mm).

Figure 45:
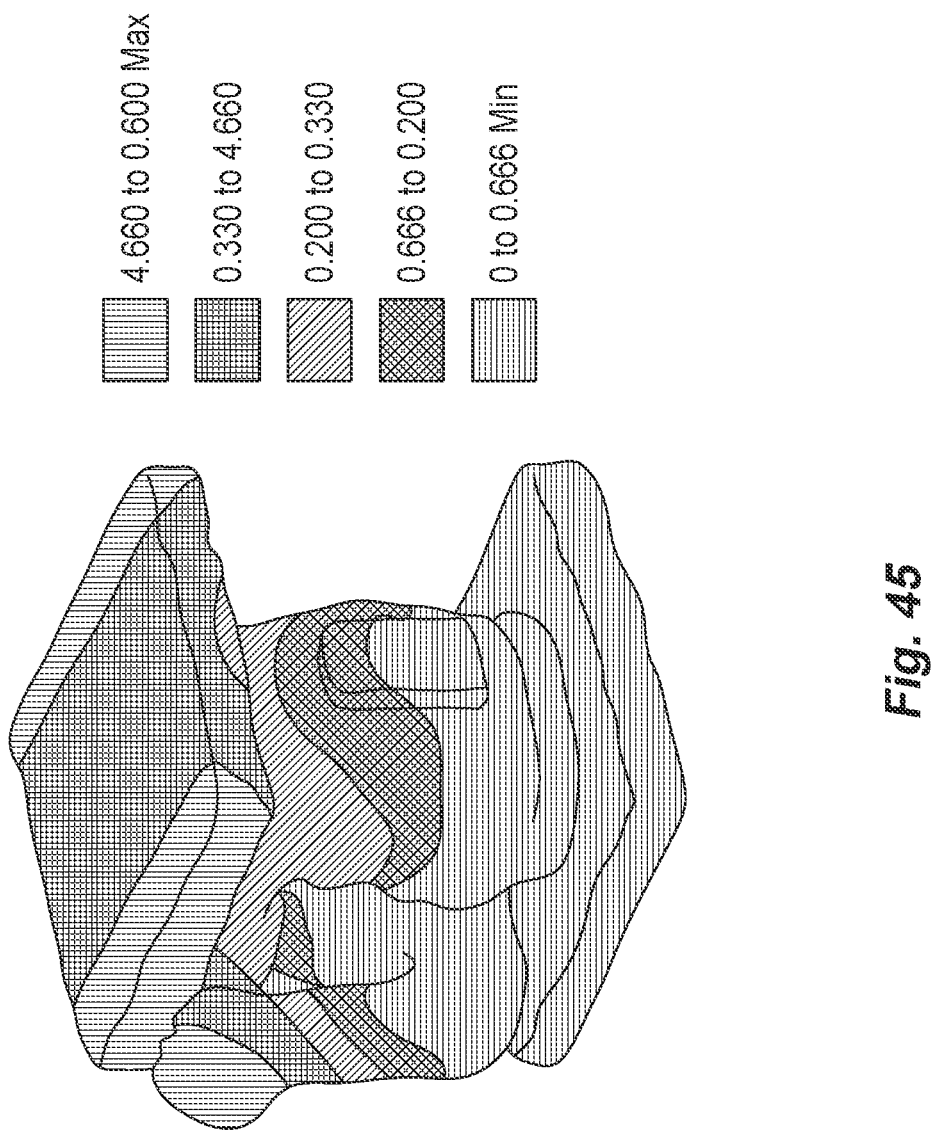
FIG. 45 shows the results of computational modeling for one embodiment of the present device under global deflection in an isometric view.

FIG. 45 shows the results of computational modeling for one embodiment of the present device under global deflection in an isometric view, for threaded plastic and total deformation (mm).

Figure 46:
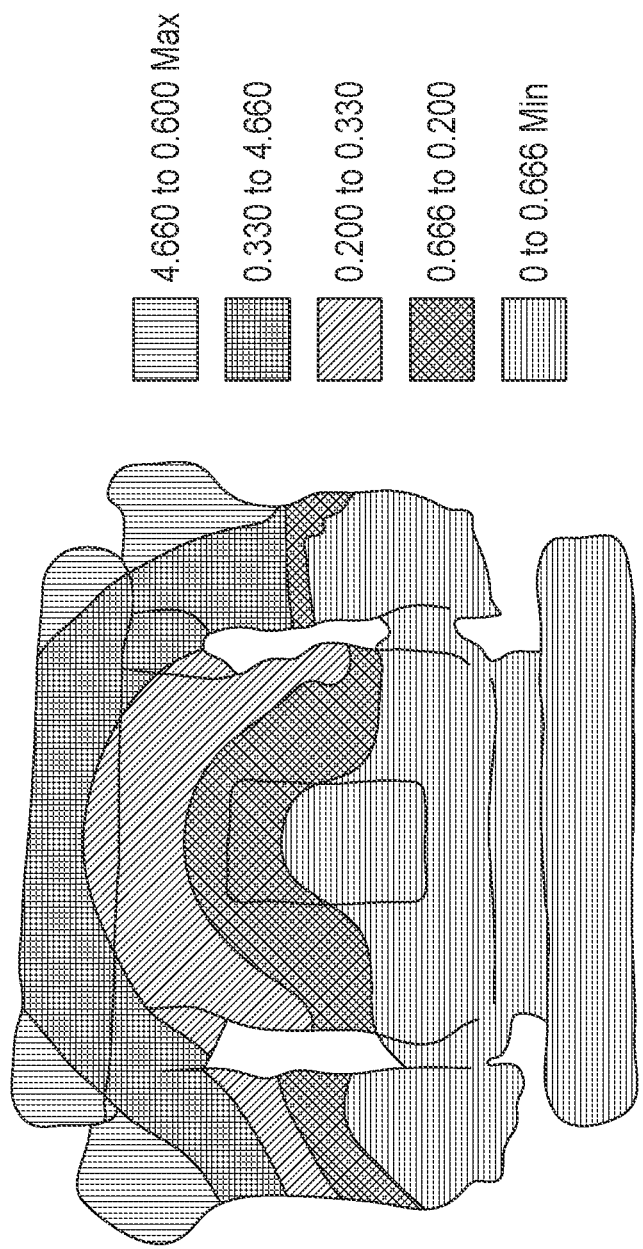
FIG. 46 shows the results of computational modeling for one embodiment of the present device under global deflection in an anterior view, PEEK composition.

FIG. 46 shows the results of computational modeling for one embodiment of the present device under global deflection in an anterior view, PEEK composition, for threaded plastic and total deformation (mm).

Figure 47:
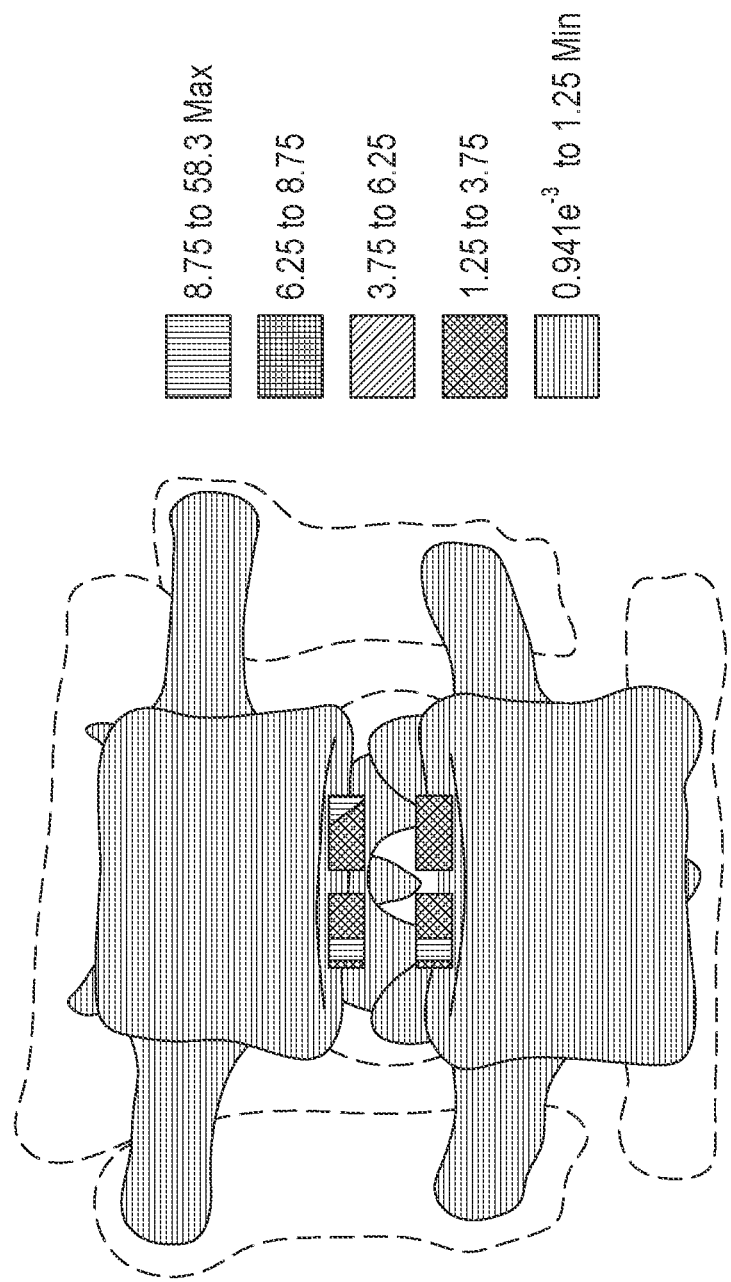
FIG. 47 shows the results of computational modeling for one embodiment of the present device under von Mises stress in an anterior view of cage graft and bone.

FIG. 47 shows the results of computational modeling for one embodiment of the present device under von Mises stress in an anterior view of cage graft and bone, for threaded plastic and equivalent von Mises stress (MPa).

Figure 48:
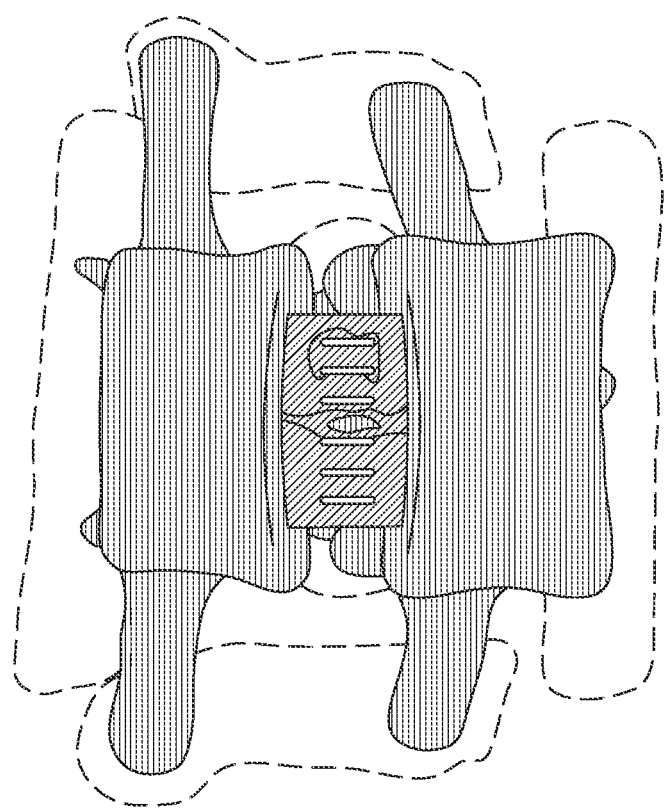
FIG. 48 shows the results of computational modeling for one embodiment of the present device under von Mises stress in an anterior view of graft bone.

FIG. 48 shows the results of computational modeling for one embodiment of the present device under von Mises stress in an anterior view of graft bone, for threaded plastic and equivalent von Mises stress (MPa).

Figure 49:
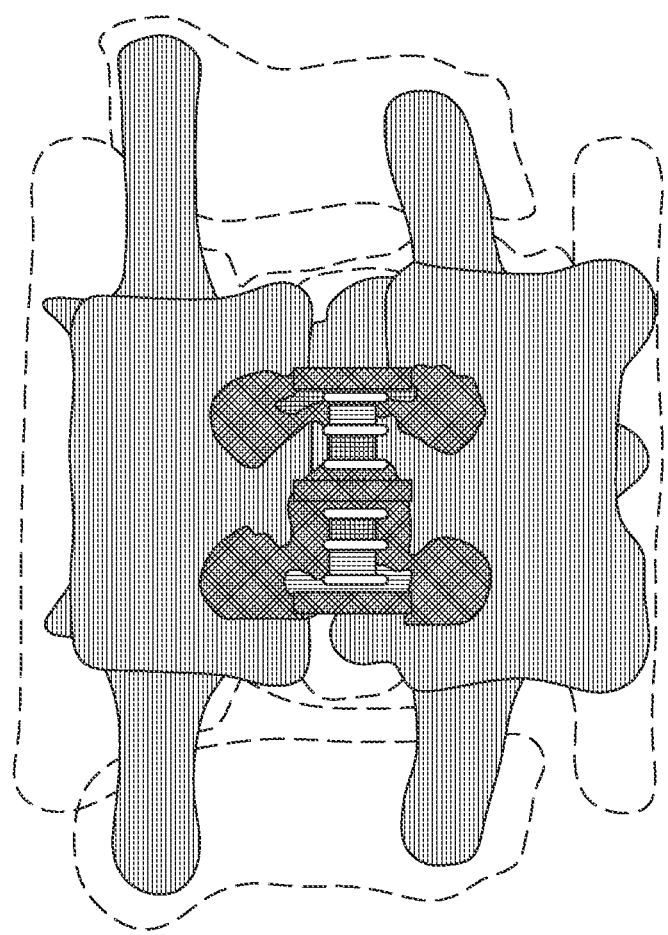
FIG. 49 shows the results of computational modeling for one embodiment of the present device under von Mises stress in a cross-sectional view of cage graft and bone.

FIG. 49 shows the results of computational modeling for one embodiment of the present device under von Mises stress in a cross-sectional view of cage graft and bone, for threaded plastic and equivalent von Mises stress (MPa).

Figure 50:
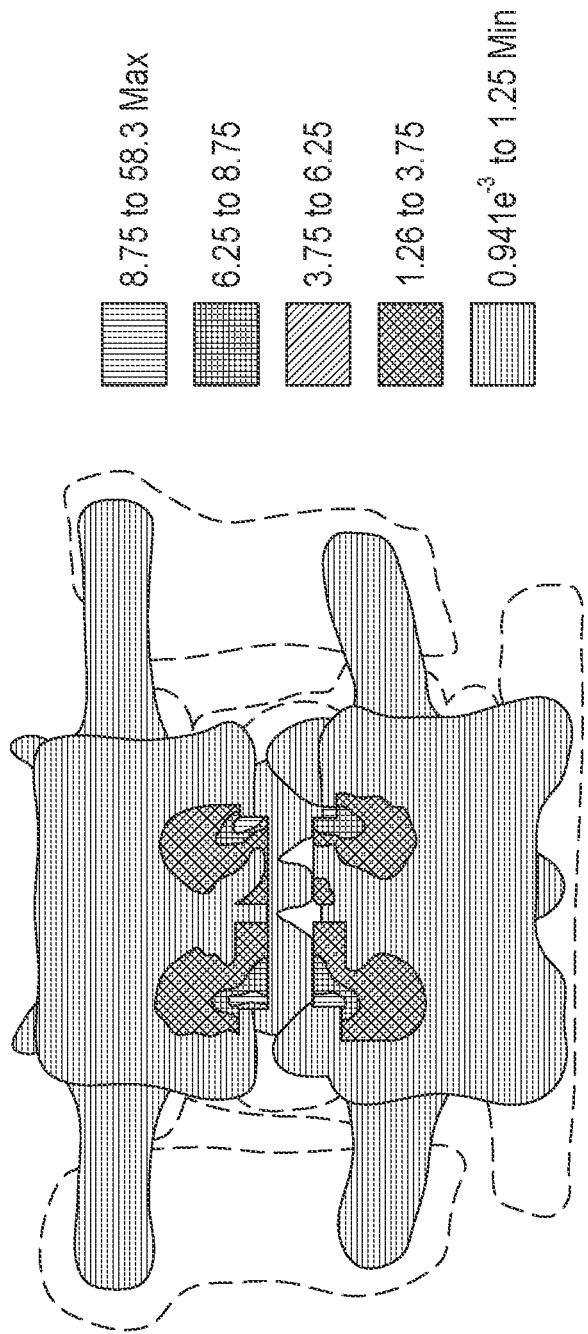
FIG. 50 shows the results of computational modeling for one embodiment of the present device under von Mises stress in a cross-sectional view of bone and graft, PEEK composition.

FIG. 50 shows the results of computational modeling for one embodiment of the present device under von Mises stress in a cross-sectional view of bone and graft, PEEK composition, for threaded plastic and equivalent von Mises stress (MPa).

Figure 51:
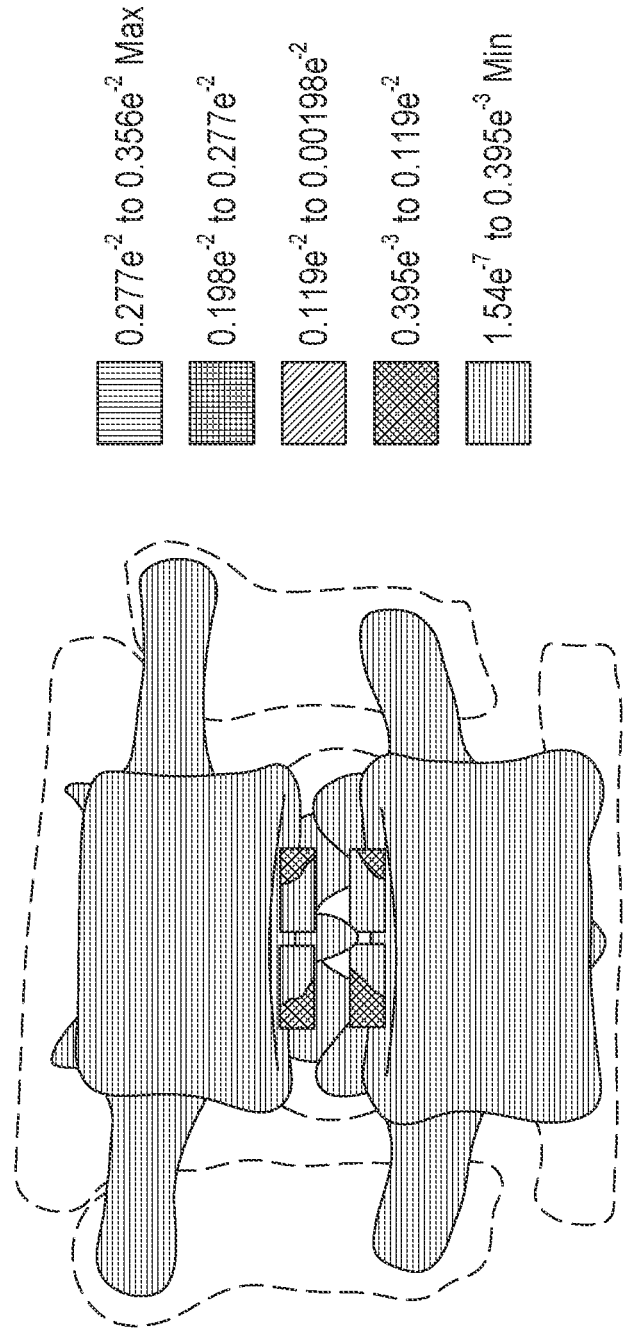
FIG. 51 shows the results of computational modeling for one embodiment of the present device under von Mises strain in a cross-sectional view of bone and graft, PEEK composition.

FIG. 51 shows the results of computational modeling for one embodiment of the present device under von Mises strain in a cross-sectional view of bone and graft, PEEK composition, for threaded plastic and equivalent elastic strain (mm/mm).

Figure 52:
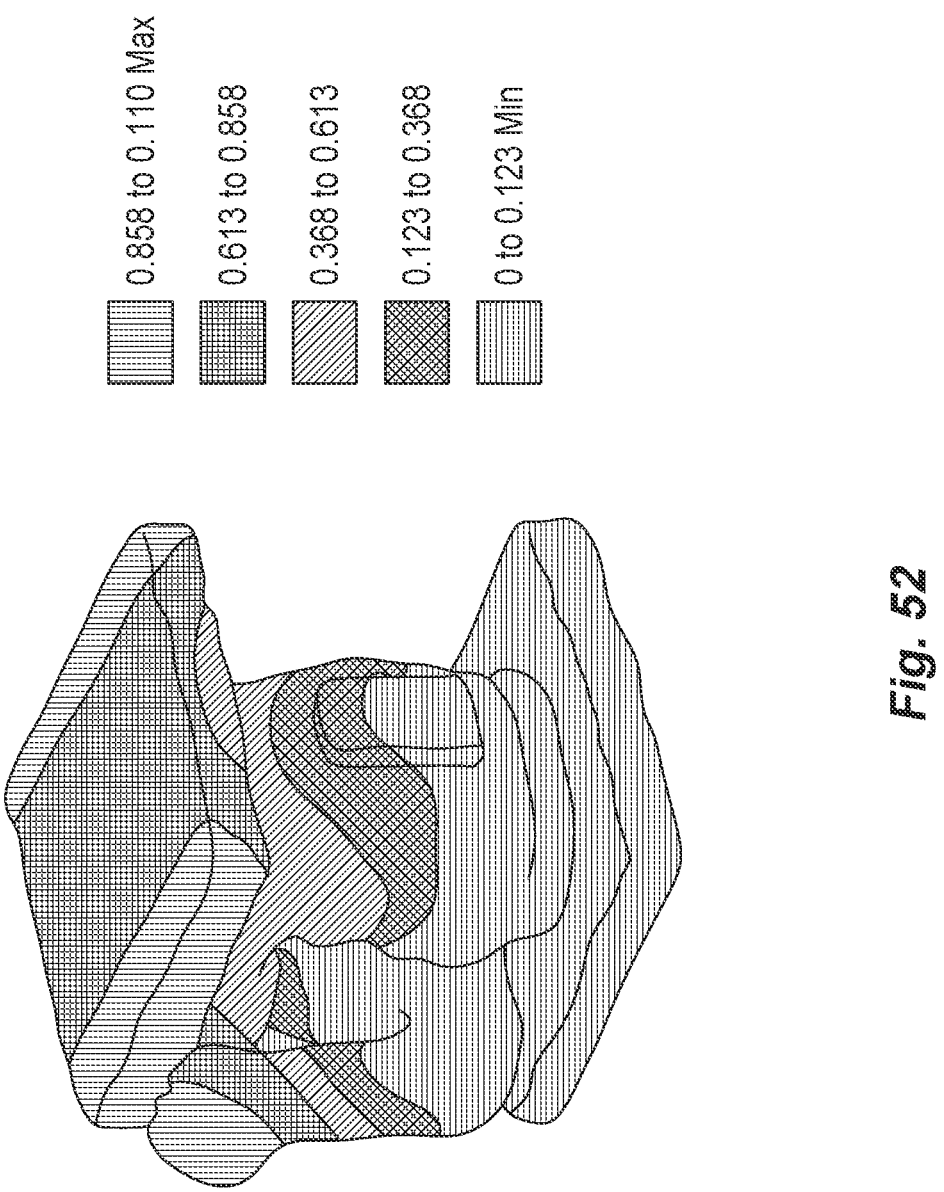
FIG. 52 shows the results of computational modeling for a further embodiment of the present device under global deflection in an isometric view, titanium composition.

FIG. 52 shows the results of computational modeling for a further embodiment of the present device under global deflection in an isometric view, titanium composition, for threaded titanium and total deformation (mm).

FIG. 53 shows the results of computational modeling for a further embodiment of the present device under global deflection in an anterior view, titanium composition, for threaded titanium and total deformation (mm).

Figure 54:
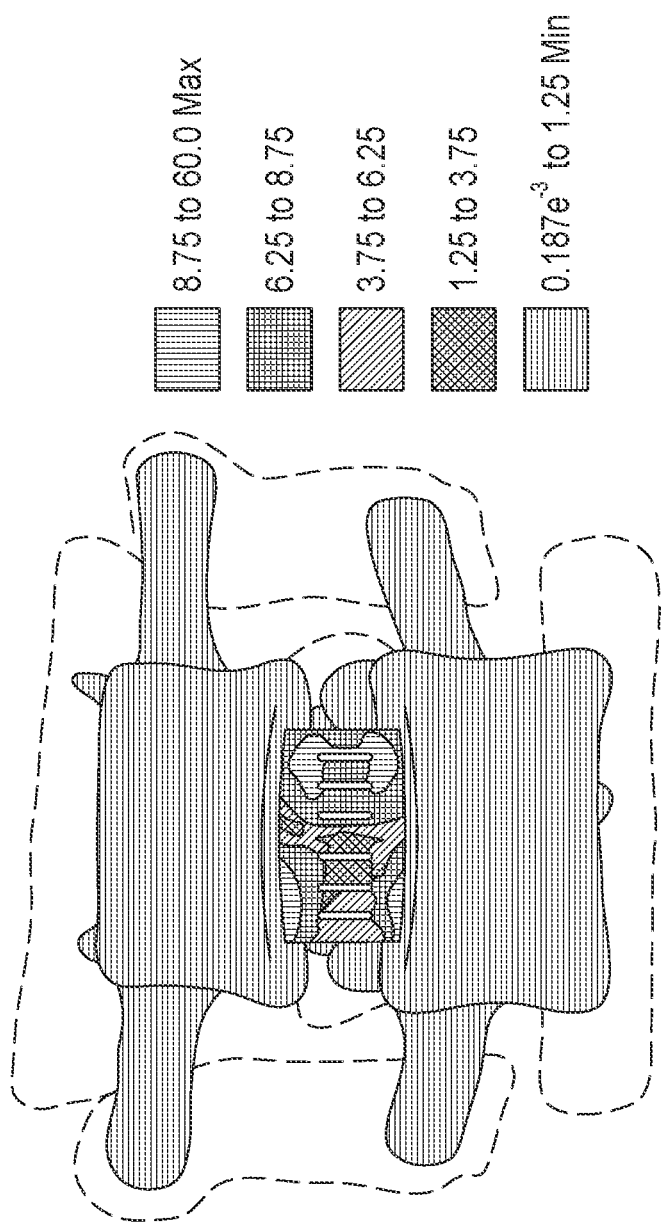
FIG. 54 shows the results of computational modeling for an embodiment of the present device under von Mises stress in an anterior view of cage graft and bone, titanium composition.

FIG. 54 shows the results of computational modeling for an embodiment of the present device under von Mises stress in an anterior view of cage graft and bone, titanium composition for threaded titanium and equivalent Von Mises Stress (MPa).

Figure 55:
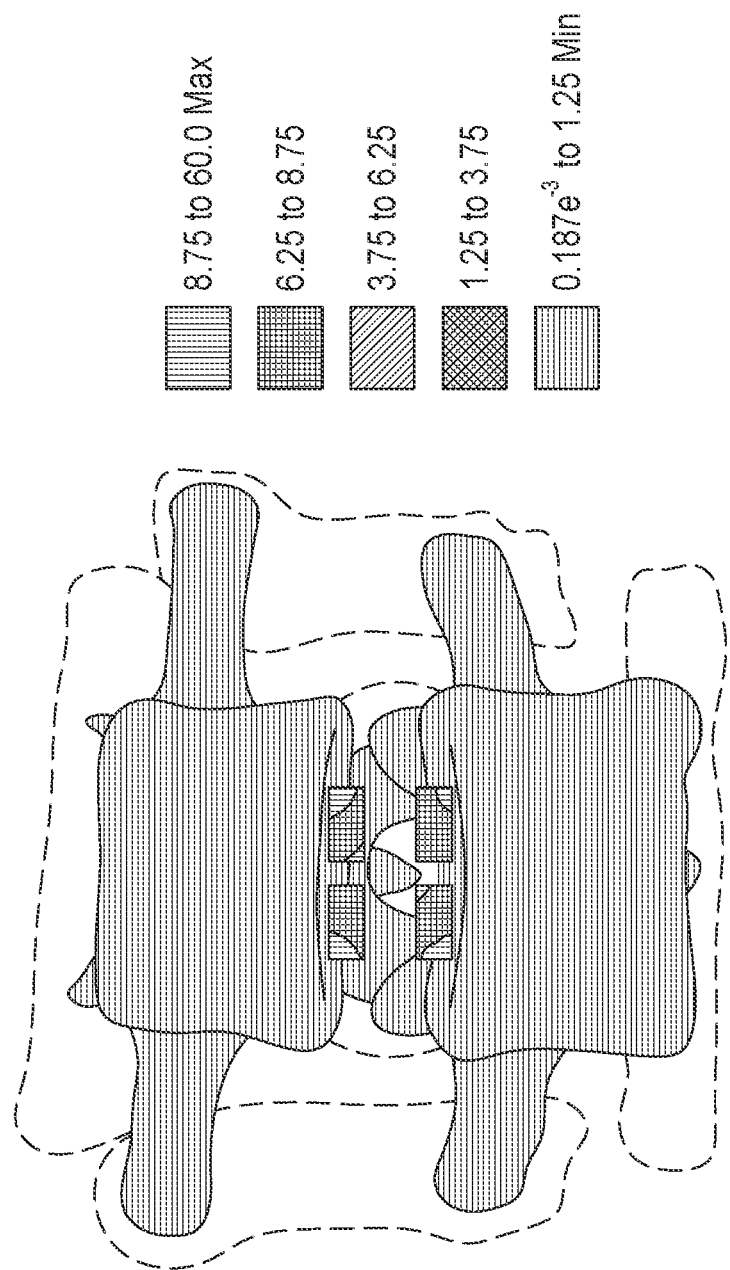
FIG. 55 shows the results of computational modeling for an embodiment of the present device under von Mises strain in an anterior view of graft and bone, titanium composition.

FIG. 55 shows the results of computational modeling for an embodiment of the present device under von Mises strain in an anterior view of graft and bone, titanium composition, for threaded titanium and equivalent Von Mises Stress (MPa).

Figure 56:
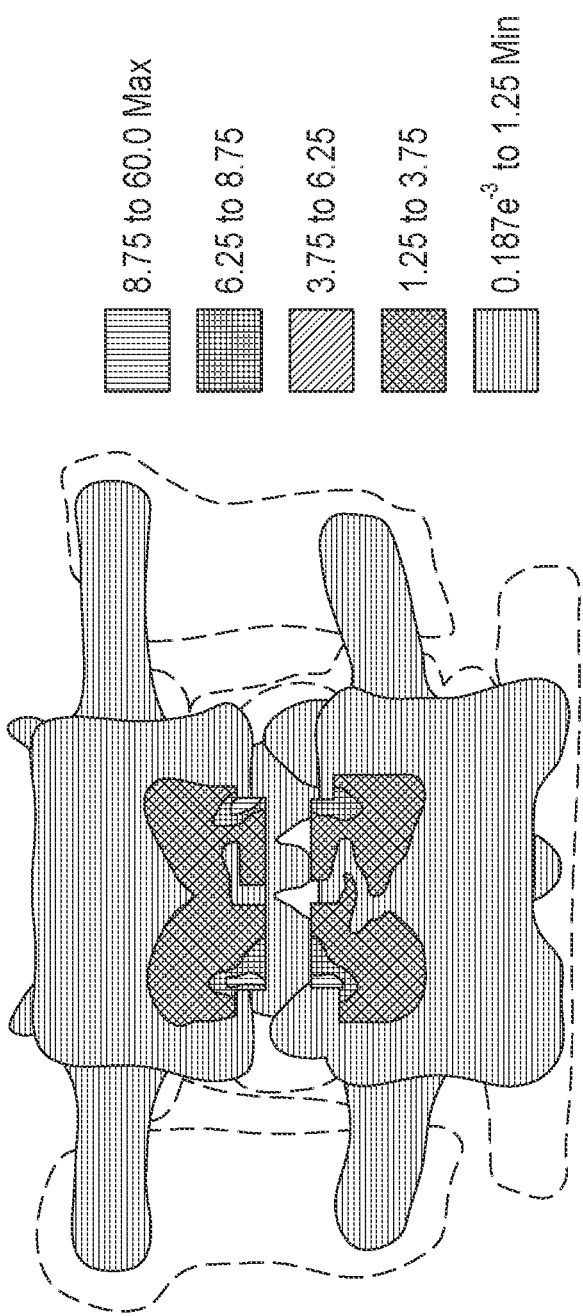
FIG. 56 shows the results of computational modeling for an embodiment of the present device under von Mises stress in a cross-sectional view of graft and bone, titanium composition.

FIG. 56 shows the results of computational modeling for an embodiment of the present device under von Mises stress in a cross-sectional view of graft and bone, titanium composition for threaded titanium and equivalent Von Mises Stress (MPa).

Figure 57:
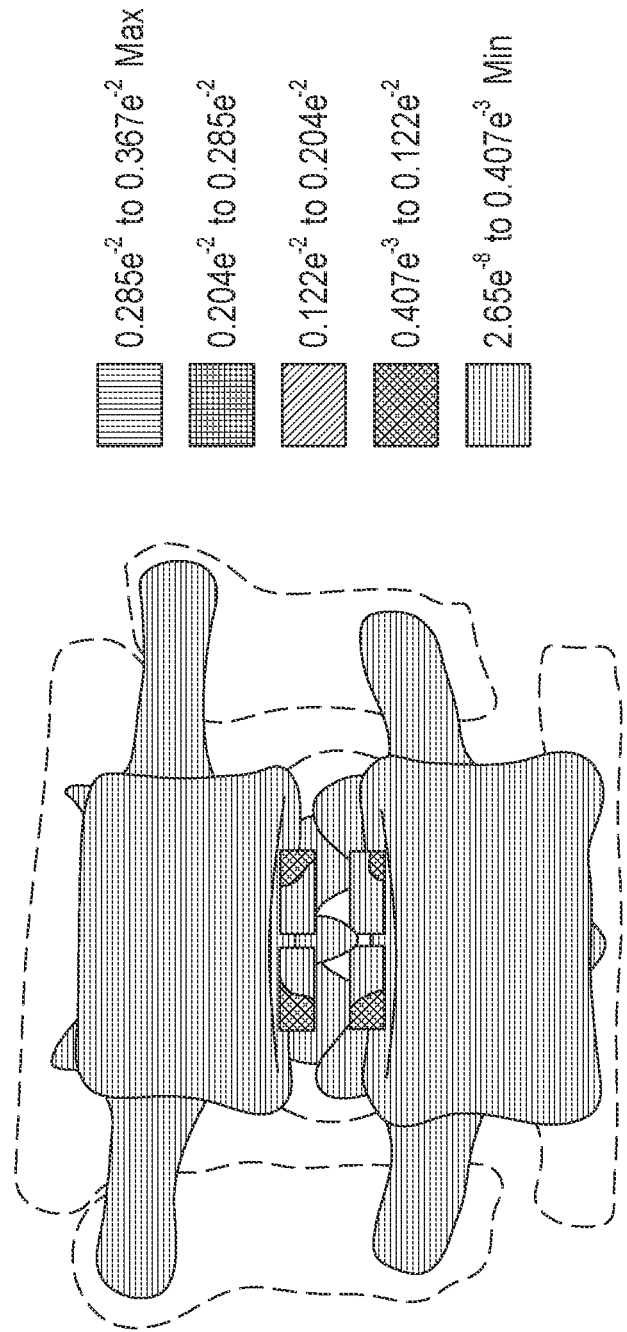
FIG. 57 shows the results of computational modeling for an embodiment of the present device under von Mises strain in a cross-sectional view of graft and bone, titanium composition.

FIG. 57 shows the results of computational modeling for an embodiment of the present device under von Mises strain in a cross-sectional view of graft and bone, titanium composition, for threaded titanium and equivalent elastic strain mm/mm.

Figure 58:
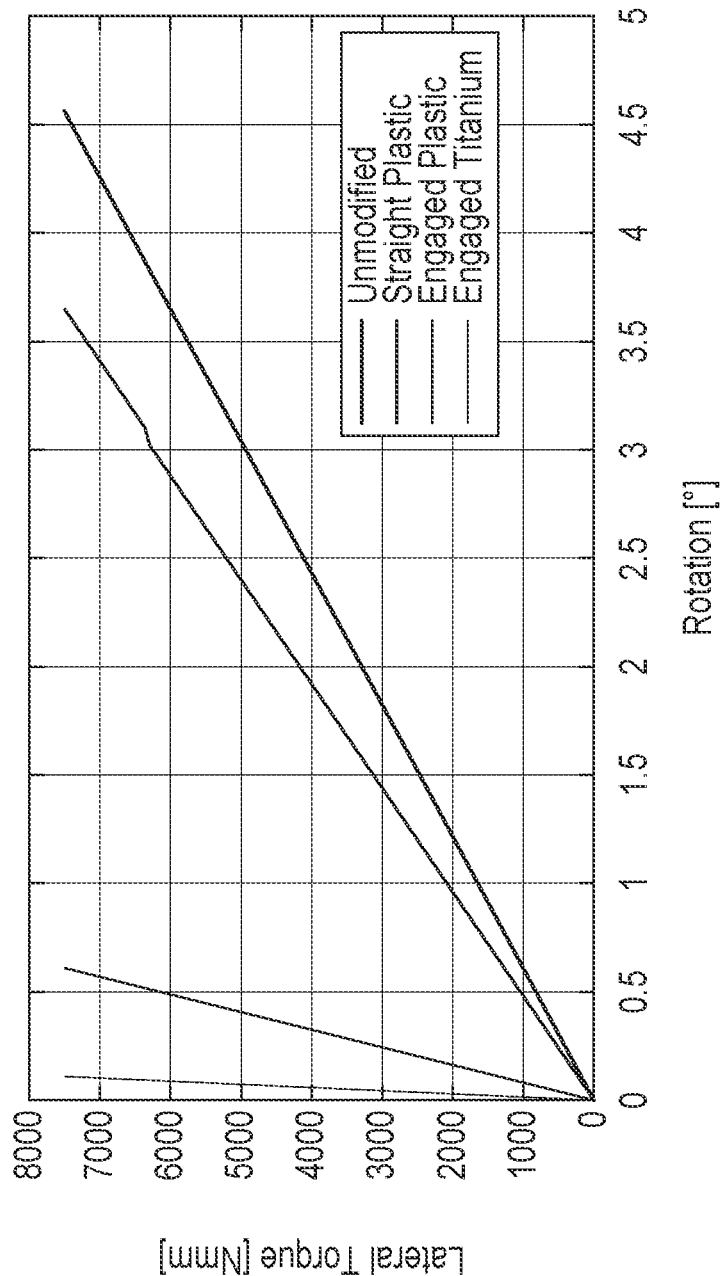
FIG. 58 shows a graph of the lateral torque compared with rotation for unmodified, conventional plastic and engaged devices of the present disclosure.

FIG. 58 shows a graph of the lateral torque compared with rotation for unmodified, conventional plastic and engaged plastic and engaged titanium devices of the present disclosure. The results are as follows.

Rotation with intact (normal spine) is 4.5 degrees

Rotation with a smooth cage with bone (but not connected between the vertebral bodies) is ~3.7 degrees. The small reduction is due impingement of the bone in the cage.

Rotation with the device of the disclosure composed of PEEK with 2 mm of engagement on each side is ~0.5 degrees.

Rotation with the device of the disclosure composed of Ti with 2 mm of engagement on each side is ~0.1 degrees.

In some forms and cases the present device may allow for symmetrical loading or may shift the loading into the graft or cage or vertebral body.

While the device has been described in reference to its preferred embodiments, it is to be understood that the words which have been used are words of description rather than limitation and that changes may be made without departing from the scope of the application as defined by the appended claims.

It is to be understood that a reference herein to a prior art document does not constitute an admission that the document forms part of the common general knowledge in the art in Australia or in any other country.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the device of the disclosure.

The invention claimed is:

1. A device for positioning between two bone regions, the device comprising:
a body configured in use to be positioned between a first bone region and a second bone region and extending along a longitudinal axis extending between the first bone region and the second bone region, the body comprising a first device end and a second device end, the second device end and the first device end being spaced apart along the longitudinal axis of the body;
a side wall extending between the first device end and the second device end, the side wall comprising an outer surface and an inner surface, the inner surface defining an interior cavity of the device,
the side wall further comprising:
a first end face extending between the outer surface and the inner surface at the first device end, the first end face defining a first outer profile where the first end face meets the outer surface and a first inner profile where the first end face meets the inner surface; and
a second end face extending between the outer surface and the inner surface at the second device end, the second end face defining a second outer profile where the second end face meets the outer surface and a second inner profile where the second end face meets the inner surface;
the inner surface of the side wall comprising a plurality of projections extending inwardly from the inner surface of the side wall into the interior cavity of the device;
the plurality of projections comprising:
a first plurality of projections extending from the inner surface into the interior cavity at the first device end, the first plurality of projections positioned at the first device end such that the inner surface and the first plurality of projections form the first inner profile;
the first plurality of projections further comprising at least one planar surface facing toward the second device end; and
a second plurality of projections extending from the inner surface into the interior cavity at the second device end, the second plurality of projections positioned at the second device end such that the inner surface and the second plurality of projections form the second inner profile;
the second plurality of projections further comprising at least one planar surface facing toward the first device end;
wherein each projection in the first plurality of projections and second plurality of projections is spaced apart laterally around an interior circumference of the inner surface from an adjacent projection in a respective plurality of projections such that in a lateral plane each of the projections is separated from an adjacent projection by the inner surface of the side wall,
wherein the first plurality of projections and second plurality of projections are configured to engage with bone growth growing into the interior cavity of the device, thereby causing the bone growth to mechanically engage and hook around the first plurality of projections and second plurality of projections.

2. The device as defined in claim 1, wherein either one of the first plurality of projections or the second plurality of projections are shaped such that bone growing from either one of the first bone region or the second bone region toward the other mechanically engages the first plurality of projections or the second plurality of projections to secure the bone growth with respect to the device and stabilise the bone region with respect to the device.

3. The device as defined in claim 2, wherein either one of the first plurality of projections or the second plurality of projections is configured to engage with bone growth that occurs through, around, onto or adjacent the plurality of projections of the device and is configured to affect mechanical engagement in more than one plane and/or in more than one vector.

4. The device as defined in claim 1, wherein the first plurality of projections includes at least one engagement surface facing the second device end and the second plurality of projections includes at least one engagement surface facing the first device end.

5. The device as defined in claim 4, wherein the engagement surfaces are angled to be perpendicular to the longitudinal axis of the device, each engagement surface being in a facing arrangement with an engagement surface on the plurality of projections at the opposing end of the device.

6. The device as defined in claim 1, wherein the device is an interbody device and the bone regions are comprised of vertebral bodies.

7. The device as defined in claim 1, wherein the interior cavity has a width and length in a lateral plane transverse to the longitudinal axis, and along the length of the interior cavity, the first inner profile of the first end face of the side wall comprises at least:
a first surface extending in line with the length of the interior cavity and the inner surface of the side wall;

a second surface projecting from the side wall into the interior cavity;

a third surface projecting from the side wall into the interior cavity to a point connected with the second surface;

a fourth surface extending in line with the length of the interior cavity and the inner surface of the side wall;

a fifth surface projecting from the side wall into the interior cavity;

a sixth surface projecting from the side wall into the interior cavity to a point connected with the fifth surface;

the second surface and third surface defining a first projection into the interior cavity and the fifth surface and sixth surface defining a second adjacent projection into the interior cavity, the projections being spaced apart along the length; and wherein the length of the first and second projections are equal to or greater than the distance the projections are spaced apart.

8. A device for positioning between two bone regions, the device comprising:

a body configured in use to be positioned between two bone regions and extending along a longitudinal axis extending between the two bone regions, the body comprising two device ends, the two device ends being spaced apart along the longitudinal axis of the body, a side wall extending between the two device ends, the side wall comprising an outer surface and an inner surface, the inner surface defining an interior cavity of the device, the side wall further comprising:

at least two end faces extending between the outer surface and the inner surface at each of the two device ends, each of the two end faces defining an outer profile where the end face meets the outer surface and an inner profile where the end face meets the inner surface; and the inner surface of the side wall comprising at least two plurality of projections extending inwardly from the inner surface of the side wall into the interior cavity of the device;

the two plurality of projections each being positioned at each of the device ends, such that the inner surface and the plurality of projections form the inner profile of the two end faces;

each projection further comprising at least one planar surface facing toward either the first or second device end, wherein each projection in the at least two plurality of projections is spaced apart laterally around an interior circumference of the inner surface from an adjacent projection in a respective plurality of projections such that in a lateral plane each of the projections is separated from an adjacent projection by the inner surface of the side wall, wherein each of the plurality of projections are configured to engage with bone growth growing into the interior cavity of the device, thereby causing the bone growth to mechanically engage and hook around the plurality of projections.

9. The device as defined in claim 8, wherein the plurality of projections extend sufficiently into the body and are positioned such that in use bone growing from one bone region toward the other results in the bone and the plurality of projections providing stabilisation of the device with respect to the bone.

10. The device as defined in claim 9, wherein the at least two plurality of projections are configured to engage with bone growth that occurs through, around, onto or adjacent the plurality of projections of the device and affects mechanical engagement in more than one plane and/or in more than one vector.

11. The device as defined in claim 8, wherein each of the plurality of projections are arranged in a plurality of sections spaced apart laterally around an interior circumference of the interior cavity such that in the lateral plane the sections are each separated by the inner surface of the side wall.

12. The device as defined in claim 11, wherein the plurality of projections each have a laterally extending surface that is positioned in a facing arrangement with a laterally extending surface of another projection.

13. The device as defined in claim 11, wherein either one of the two plurality of projections comprises a region that is angled with respect to the longitudinal axis of the device.

14. The device as defined in claim 11, wherein either one of the plurality of projections is in the form of surface profiles, shoulders or sloped regions.

15. The device as defined in claim 11, wherein either one of the plurality of projections is in the form of plates, ridges, wires, or protrusions of various geometric arrangements extending from the device or in the form of depressions or apertures.

16. The device as defined in claim 11, wherein each of the plurality of sections includes some of the plurality of projections that are aligned with one another in the longitudinal direction.

17. The device as defined in claim 16, wherein each of the plurality of projections includes a laterally extending surface.

18. The device as defined in claim 11, wherein at least one of the two opposing device ends includes a bone facing surface, and the bone facing surface has an outlined shape from at least one side.

* * * * *